(12) United States Patent
Wanasek et al.

(10) Patent No.: US 7,096,063 B2
(45) Date of Patent: *Aug. 22, 2006

(54) METHOD AND APPARATUS FOR DELIVERING MULTI-DIRECTIONAL DEFIBRILLATION WAVEFORMS

(75) Inventors: Kevin A. Wanasek, Princeton, MN (US); William J. Havel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 115 days.

This patent is subject to a terminal disclaimer.

(21) Appl. No.: 10/804,780

(22) Filed: Mar. 19, 2004

(65) Prior Publication Data

US 2005/0209647 A1    Sep. 22, 2005

(51) Int. Cl.
*A61N 1/39* (2006.01)
(52) U.S. Cl. .............................. 607/5; 607/7; 128/898
(58) Field of Classification Search .................... 607/4, 607/5, 7; 128/898
See application file for complete search history.

(56) References Cited

U.S. PATENT DOCUMENTS

| | | | |
|---|---|---|---|
| 4,316,472 A | 2/1982 | Mirowski et al. | |
| 4,384,585 A | 5/1983 | Zipes | |
| 4,566,457 A * | 1/1986 | Stemple ......................... | 607/5 |
| 4,587,970 A | 5/1986 | Holley et al. | |
| 4,641,656 A | 2/1987 | Smits | |
| 4,708,145 A | 11/1987 | Tacker et al. | |
| 4,726,379 A * | 2/1988 | Altman et al. .................. | 607/9 |
| 4,726,380 A | 2/1988 | Vollmann et al. | |
| 4,727,877 A | 3/1988 | Kallok | |
| 4,830,006 A | 5/1989 | Haluska et al. | |
| 4,850,357 A | 7/1989 | Bach | |
| 4,932,407 A | 6/1990 | Williams | |
| 4,949,719 A | 8/1990 | Pless et al. | |
| 4,953,551 A | 9/1990 | Mehra et al. | |
| 4,998,531 A | 3/1991 | Bocchi et al. | |
| 5,107,834 A | 4/1992 | Ideker et al. | |
| 5,117,824 A | 6/1992 | Keimel et al. | |
| 5,163,427 A | 11/1992 | Keimel | |
| 5,188,105 A | 2/1993 | Keimel | |
| 5,376,105 A * | 12/1994 | Hedberg ......................... | 607/5 |
| 5,405,361 A * | 4/1995 | Persson ......................... | 607/5 |
| 5,411,524 A | 5/1995 | Rahul | |
| 5,441,518 A * | 8/1995 | Adams et al. .................. | 607/5 |
| 5,468,254 A | 11/1995 | Hahn et al. | |

(Continued)

OTHER PUBLICATIONS

Pagan-Carlo MD et al. "Encircling Overlapping Multipulse Shock Waveforms for Transthoracic Defibrillation" *J of Am Coll Cardio*. Dec. 1998;vol. 32 Issue 7:pp. 2065-2071.

*Primary Examiner*—Robert E. Pezzuto
*Assistant Examiner*—Brian T. Gedeon
(74) *Attorney, Agent, or Firm*—Michael C. Soldner; Girma Wolde-Michael

(57) ABSTRACT

A method and device for delivering a pulse waveform to a target site of a patient that includes an energy storage device storing electrical energy, and a plurality of electrodes electrically coupled to the energy storage device. Control circuitry, coupled to a plurality of switching elements coupled to the plurality of electrodes, selectively switches the plurality of switching elements between a first state and a second state to direct discharge of the stored energy to be simultaneously output at selected electrodes of the plurality of electrodes to generate discrete sequential resultant output pulses across multiple pathways, the discrete sequential resultant output pulses generating a multi-directional waveform at the target site.

34 Claims, 15 Drawing Sheets

U.S. PATENT DOCUMENTS

| | | | |
|---|---|---|---|
| 5,620,469 A * | 4/1997 | Kroll | 607/7 |
| 5,653,740 A | 8/1997 | Degroot et al. | |
| 6,091,988 A | 7/2000 | Warman et al. | |
| 6,298,266 B1 * | 10/2001 | Rubin et al. | 607/5 |
| 6,647,292 B1 | 11/2003 | Bardy et al. | |
| 6,668,193 B1 * | 12/2003 | Ware et al. | 607/5 |
| 2002/0095187 A1 | 7/2002 | Thompson et al. | |

* cited by examiner

METHOD AND APPARATUS FOR DELIVERING MULTI-DIRECTIONAL DEFIBRILLATION WAVEFORMS

RELATED APPLICATION

Cross-reference is hereby made to commonly assigned related U.S. applications Ser. No. 10/804,322, filed concurrently herewith, entitled "METHOD AND APPARATUS FOR DELIVERING MULTI-DIRECTIONAL DEFIBRILLATION WAVEFORMS", incorporated herein by reference in its entirety.

FIELD OF THE INVENTION

The present invention relates generally to cardiac defibrillation devices and, more specifically, to a system and method for defibrillating the heart using multiple-pathway, simultaneously delivered phase-shifted waveforms for achieving a multi-directional defibrillation vector field.

BACKGROUND OF THE INVENTION

Implantable systems for delivering high-energy shocks to defibrillate the heart conventionally use single or multiple simultaneous or sequential electrode vectors to deliver a defibrillation waveform. A single electrode vector, for example, between an electrode located in the right ventricle and an electrode placed outside the right ventricle, often results in undesirably high energy levels being required in order to effectively defibrillate the heart (defibrillation threshold). In delivering a defibrillation shock, it is desirable to deliver the energy in a vector substantially parallel to a large mass of the cardiac myocytes in order to simultaneously depolarize the myocytes and "reset" the timing of myocyte firing, thereby restoring normal sinus rhythm. This shock directionality is approximated through the positioning of defibrillation electrodes relative to the heart. However, because the cardiac structure is complex, a defibrillation pathway selected between two defibrillation coil electrodes, between a defibrillation coil electrode and the implantable device housing used as a "CAN" electrode, or between a defibrillation coil electrode and a subcutaneous patch electrode, may be substantially parallel to a limited cell population.

In an effort to reduce the amount of energy required to effect defibrillation, numerous suggestions have been made with regard to multiple electrode systems. For example, sequential pulse multiple electrodes systems are generally disclosed in U.S. Pat. No. 4,708,145 issued to Tacker et al., U.S. Pat. No. 4,727,877 issued to Kallok et al., U.S. Pat. No. 4,932,407 issued to Williams et al., and U.S. Pat. No. 5,163,427 issued to Keimel.

An alternative approach to multiple electrode sequential pulse defibrillation is disclosed in U.S. Pat. No. 4,641,656 to Smits and also in the above-cited Williams patent. An alternative multiple electrode, simultaneous pulse system is disclosed in U.S. Pat. No. 4,953,551, issued to Mehra et al., employing right ventricular, superior vena cava and subcutaneous patch electrodes.

Pulse waveforms delivered either simultaneously or sequentially to multiple electrode systems may be monophasic (either of positive or negative polarity), biphasic (having both a negative-going and positive-going pulse), or multiphasic (having two or more polarity reversals). Such waveforms thus include one or more pulses of negative and/or positive polarity that are typically truncated exponential pulses. While the term "multiphasic" is used to refer to a pulse waveform having two or more polarity reversals, the waveform may be described as a "multiple pulse" waveform that includes both positive and negative pulses with intervening pulse delays. These monophasic, biphasic, and multiphasic pulse waveforms are achieved by controlling the discharge of a capacitor or bank of capacitors during shock delivery.

Simultaneous multiple electrode defibrillation configurations provide a defibrillation pathway along more than one vector simultaneously producing a net vector field. However, in multiple electrode configurations, each pathway or vector will have an associated resistance. When multiple pathways are used simultaneously, a current divider effect is created. The path with the least resistance will receive the majority of the defibrillation shock current.

In sequential multiple electrode configurations, a defibrillation waveform is typically delivered along two current pathways sequentially such that one defibrillation vector is produced followed by a second defibrillation vector. The directionality of the sequential vectors is generally limited to two distinct vectors determined by the location of the electrodes used to deliver each pulse. Even when using multiple electrode configurations, a relatively high-energy shock is still required in order to successfully defibrillate the heart.

Reducing device size to an acceptable implantable size was a major obstacle in realizing the first implantable defibrillation devices. Large battery and capacitor requirements for delivering high-energy shock pulses required early devices to be relatively large. Using truncated biphasic exponential waveforms for internal cardiac defibrillation via transvenously positioned electrodes has allowed defibrillation thresholds to be reduced to the point that device size is acceptable for pectoral implant. However, relatively high energy requirements still continue to limit device longevity and size reduction, both of which continue to be motivating factors to improve implantable defibrillation systems by reducing the defibrillation thresholds required to successfully defibrillate the heart. Reduced defibrillation energy may also reduce sensitivity to lead placement and differences in cardiac anatomy and thereby reduce the number of patients in which unacceptable defibrillation thresholds are encountered.

As discussed previously, reduction in defibrillation thresholds may be achievable if a greater number of the cardiac myocytes are parallel to the defibrillation vector field. One approach to addressing this need could be to increase the number of electrodes to allow delivery of simultaneous or sequential defibrillation pulses along a greater number of vectors. Placement of additional electrodes however, adds size, cost, and complexity to the implanted system and would make implantation of the system an arduous task.

There remains a need, therefore, for an improved system and method for defibrillating the heart using a multi-directional defibrillation vector field for achieving successful defibrillation at lower shock energies and that allows a reduction in implantable device size and/or extension of the useful life of the implanted device. By reducing the defibrillation energy required, the number of patients in which acceptable defibrillation thresholds are unachievable may also be reduced.

BRIEF SUMMARY OF THE INVENTION

The present invention provides a system and method for delivering defibrillation waveforms in a multi-directional vector field using simultaneously delivered signals along multiple electrode pathways. The multi-directional field may vary in direction in a continuous manner, produced by delivering a continuous, phase-shifted defibrillation waveform. Alternatively, the multi-directional field may vary in direction in discrete steps produced by delivering a stepped defibrillation waveform.

The system includes a defibrillation device coupled to at least three electrodes wherein the device includes a high voltage capacitor or bank of capacitors for storing electrical energy; control circuitry for generating control signals; and pulse generating circuitry responsive to the control signals. The pulse generating circuitry includes an output bridge circuit having at least three legs wherein each leg includes a pair of switching elements and an output terminal coupled to a respective electrode. In an alternative embodiment, two legs each having a pair of switching elements and an output terminal are provided with the third output terminal serving as a reference terminal for the other two. The switching elements included in the output bridge circuit are selectively opened and closed in response to control signals to produce pulse signals during capacitor discharge. In an external system, pulses may be generated during capacitor discharge or, alternatively, line power may be used to provide a voltage signal across each bridge leg.

In one embodiment, a continuous multi-directional defibrillation vector field is achieved by delivering a phase-shifted defibrillation waveform. The phase-shifted defibrillation waveform includes multiple signals shifted in phase from each other. The multiple phase-shifted signals are delivered simultaneously to multiple defibrillation pathways via the output terminals of the output bridge circuit wherein each signal delivered to each output terminal is shifted in phase from at least one other signal delivered to another output terminal. Phase-shifted sine wave signals or sine wave signals approximated by a chopped waveform may be simultaneously delivered to multiple pathways. The resultant multi-directional vector field will be a continuously rotating vector field.

An approximated sinusoidal, phase-shifted defibrillation waveform may be achieved by generating a pulse width modulated (PWM) signal at each output terminal of the output bridge with each PWM signal shifted in phase with respect to the other PWM signals. In other embodiments, a phase-shifted defibrillation waveform used for achieving a continuous multi-directional vector field may be formed by generating two or more signals that ramp and decay, signals that exponentially rise and fall, or other continuous phasic signal morphologies wherein the signals are shifted in phase from each other.

In another embodiment, an approximated sinusoidal, phase-shifted defibrillation waveform is achieved by further including a choke element in each leg of the output bridge circuit for smoothing a pulse width modulated signal. A smoothed sinusoidal signal is produced at each output terminal. The sinusoidal signal at a given output terminal is shifted in phase with respect to the sinusoidal signals at the other output terminals. Choke elements may be included in the output bridge circuitry within the defibrillation device or be implemented external to the device. For example, a choke element could be implemented in the leads carrying the defibrillation electrodes.

In yet another embodiment, a multi-directional defibrillation waveform is delivered using multiple stepped signals delivered simultaneously to multiple pathways produced by controlling switching elements in a selected number of steps. The order and number of switching steps control the directionality of a discrete multi-directional vector field. The discrete multi-directional vector field may change directions in a stepwise rotating, alternating, or random manner through control of the switching steps. In one embodiment, a six-step control algorithm is applied to selectively open and close the switching elements to generate a stepped, truncated, exponential defibrillation waveform. Stepped, truncated exponential signals are delivered simultaneously to multiple pathways, such that the directionality of a net defibrillation vector during each step is changed. The six switching steps may be performed in a manner so as to generate a resultant vector field that rotates or alternates in a random or ordered sequence.

In another embodiment, an eleven-step control algorithm is applied to selectively open and close the switching elements to generate a stepped, truncated exponential waveform that creates a discrete multi-directional vector field which may rotate stepwise in a first direction then rotate stepwise in a second direction.

In yet another embodiment, a twelve-step control algorithm is applied to selectively open and close switching elements which includes switching delays to allow sequential selection of multiple pathways and single pathways. By sequentially selecting multiple pathways and single pathways, additional vectors are available in a discrete, multi-directional vector field. Any number of steps may be included in a stepped defibrillation waveform to create a discrete multi-directional defibrillation vector field that changes directionality in a generally rotating, alternating, random, or other spatial pattern.

BRIEF DESCRIPTION OF THE DRAWINGS

Aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1A:
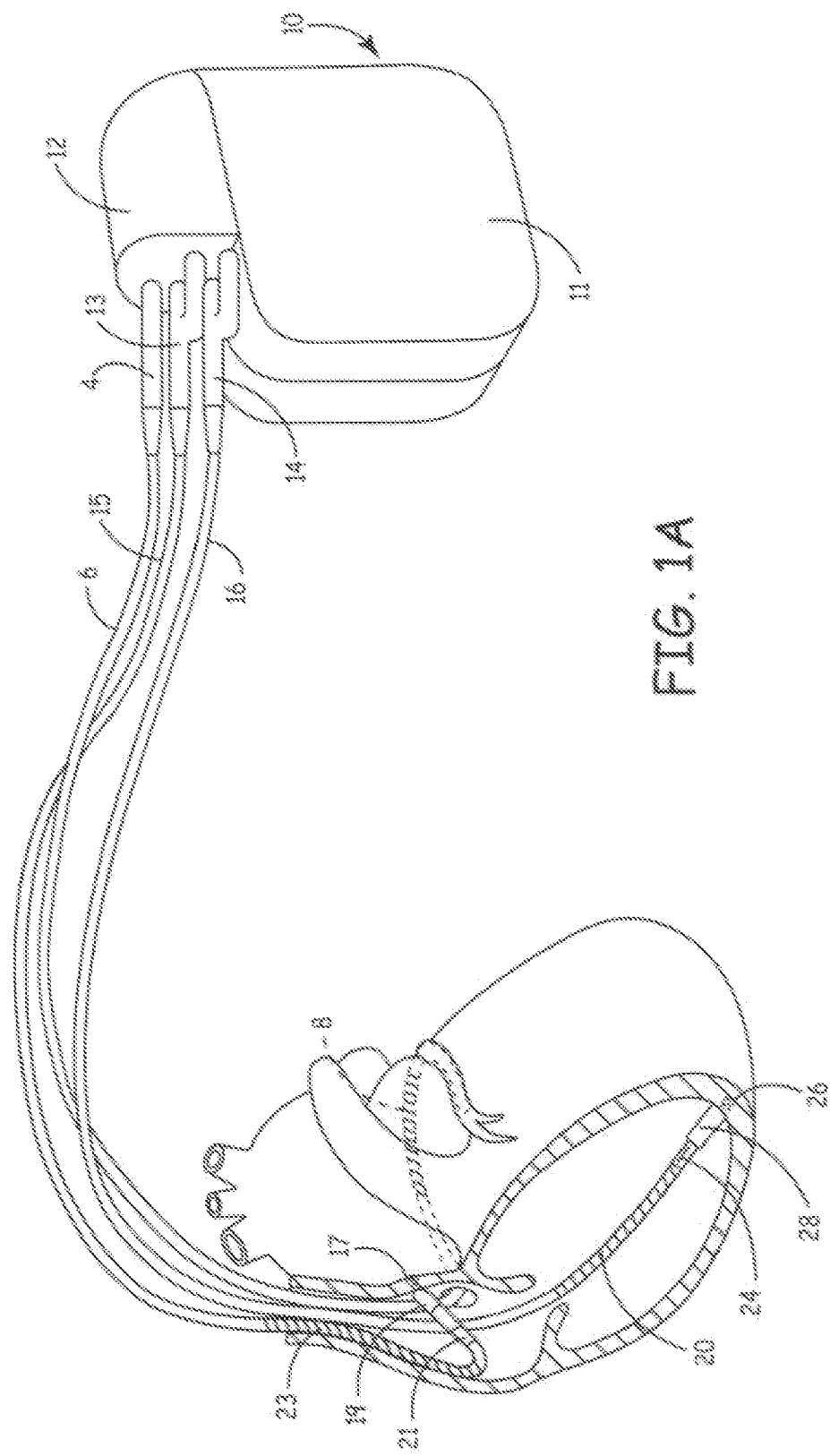
FIG. 1A is an illustration of an exemplary implantable cardiac stimulation device coupled to transvenous leads.

The present invention is directed toward providing a system and method for cardioverting or defibrillating the heart using a defibrillation waveform that includes multiple signals delivered simultaneously to multiple electrode pathways to create a dynamically varying, multi-directional defibrillation vector field. The defibrillation waveform may be composed of continuous, phase-shifted signals delivered simultaneously to multiple electrode pathways to achieve a continuous or "sweeping" multi-directional vector field. Alternatively, the defibrillation waveform may be composed of stepped signals delivered simultaneously to multiple pathways to achieve a discrete multi-directional vector field.

"Cardioversion" typically refers to the termination of tachycardia, and "defibrillation" typically refers to the termination of fibrillation. When not stated otherwise, the terms "defibrillation" and "defibrillator" are intended to include "cardioversion" and "cardioverter", respectively, in that the multi-directional defibrillation waveforms produced in accordance with the present invention may be duly used whenever a high-energy shock therapy is required, including both cardioversion and defibrillation shock therapies.

The present invention reduces defibrillation thresholds, improves defibrillation success rate, reduces sensitivity to electrode location, and results in fewer cases of unattainable acceptable defibrillation thresholds. In one embodiment, the present invention is implemented in an implantable cardiac defibrillation device. The overall device size may be reduced by reducing battery and capacitor size, thereby allowing for greater patient comfort and acceptance, and/or the useful life of the implantable device may be extended due to reduced defibrillation thresholds. A reduction in defibrillation thresholds which reduces the delivered voltage requirements of the device reduces space requirements for implementing output circuitry. The standoff voltage required in output circuitry of currently available high-voltage devices requires a relatively large amount of the available volume within the implantable device. Utilizing the present invention t reduce the delivered voltage requirements will reduce the space requirements for the output circuitry, allowing overall device size reduction or allowing increased battery size, memory size or other device enhancements. Implantable systems in which the present invention may be usefully practiced include single, dual or multi-chamber systems used for defibrillating the atrial and/or the ventricular heart chambers.

Multi-chamber implantable systems will be described in detail herein to illustrate various embodiments of the present invention. The advantages provided by the present invention, however, can also be beneficial in external defibrillation systems. As such, aspects of the present invention may be advantageously employed in external defibrillation systems utilizing cutaneous or transcutaneous electrode systems.

FIG. 1A is an illustration of an exemplary implantable cardiac stimulation device in which the present invention may be practiced. Device 10 is provided with multi-chamber pacemaking, cardioversion, and defibrillation capabilities and is coupled to a patient's heart by way of multiple leads. For example, a connector block 12 receives the proximal end of a right ventricular lead 16, a right atrial lead 15 and a coronary sinus lead 6, used for positioning electrodes for sensing and stimulation in three or four heart chambers.

In FIG. 1A, the right ventricular lead 16 is positioned such that a distal end is in the right ventricle (RV) for sensing right ventricular cardiac signals and delivering pacing or shocking pulses in the right ventricle. For these purposes, right ventricular lead 16 includes a ring electrode 24, a tip electrode 26, optionally mounted retractably within an electrode head 28, and an RV coil electrode 20, each of which are connected to an insulated conductor contained within the body of lead 16. The proximal end of the insulated conductors are coupled to corresponding connectors carried by connector 14 at the proximal end of lead 16 for providing electrical connection to the device 10, referred to hereafter as "implantable cardioverter defibrillator" or "ICD".

The right atrial lead 15 is positioned such that a distal end is in the vicinity of the right atrium and the superior vena cava (SVC). Lead 15 includes a ring electrode 21 and a tip electrode 17, optionally mounted retractably within electrode head 19, for sensing and pacing in the right atrium. Lead 15 further includes an SVC coil electrode 23 for delivering high-energy shock therapy. The ring electrode 21, the tip electrode 17 and the SVC coil electrode 23 are each connected to an insulated conductor with the body of the right atrial lead 15. Each insulated conductor is coupled at a proximal end to a connector carried by connector 13.

The coronary sinus (CS) lead 6 is advanced within the vasculature of the left side of the heart via the coronary sinus and great cardiac vein and may be advanced further into a deeper cardiac vein. The coronary sinus lead 6 is shown in the embodiment of FIG. 1A as having a defibrillation coil electrode 8 that may be used in combination with either or both the RV coil electrode 20 or the SVC coil electrode 23 for delivering electrical shocks for cardioversion and defibrillation therapies. The device housing 11 may also serve as a subcutaneous defibrillation electrode in combination with two or more of the defibrillation coil electrodes 8, 20 or 23 for defibrillation of the atria and/or ventricles. In other embodiments, CS lead 6 may also include a distal tip electrode and ring electrode for pacing and sensing functions in the left chambers of the heart. The CS coil electrode 8 is coupled to an insulated conductor within the body of lead 6, which provides connection to the proximal connector 4.

It is recognized that alternate lead systems may be substituted for the three lead system illustrated in FIG. 1A. The present invention employs at least three electrodes for delivering a phase-shifted or stepped defibrillation waveform for achieving a dynamically-varying multi-directional vector field. While three coil electrodes 8, 20 and 23 shown in FIG. 1A are each located on separate leads, other lead systems could be substituted that include two or more defibrillation coils on a single lead. For example, a quadrapolar lead having an RV tip electrode, an RV ring electrode, an RV coil electrode and an SVC coil electrode may be used.

The approximate positions of electrodes 8, 20 and 23 and can 11 as shown in FIG. 1 are illustrative. Multiple electrode pathways for delivering defibrillation waveforms in accordance with the present invention may be selected between coil electrodes 8, 20 and 23, or may alternatively include can 11 in combination with two or three of the coil electrodes 8, 20 or 23. In some embodiments, can 11 may be electrically coupled to the same potential as one of the coil electrodes 8, 20 or 23. When 3-electrode configurations are used, the triangle formed by the three electrodes preferably encompasses a large volume of the targeted cardiac chamber(s).

According to another embodiment of the present invention, an electrode configuration including RV coil 20, can 11, CS coil 8 and/or a coronary vein (CV) coil electrode could be utilized. CV coil 8 and the CV coil electrode could be utilized in conjunction with a pacing lead as electrically separate electrodes, tied together, or tied to RV coil 20 or can 11. In the dual coil configuration, a distal coil would be positioned within the coronary vein and a proximal coil would be positioned in the coronary sinus, and may be partially within the right atrium or the superior vena cava.

While a particular multi-chamber ICD and lead system is illustrated in FIG. 1, methodologies included in the present invention may be adapted for use with other single chamber, dual chamber, or multichamber ICD systems involving multiple defibrillation electrodes located within the heart or external to the heart such as epicardial or subcutaneous placements. The implementation of the present invention may also include a device that does not employ cardiac leads as described above to detect and treat arrhythmias. For example, a device implanted subcutaneously or sub-muscularly in a position over the heart such as an axillary location could use non-intracardiac lead based methods for delivering electrical stimulation therapies and sensing cardiac activity.

Figure 1B:
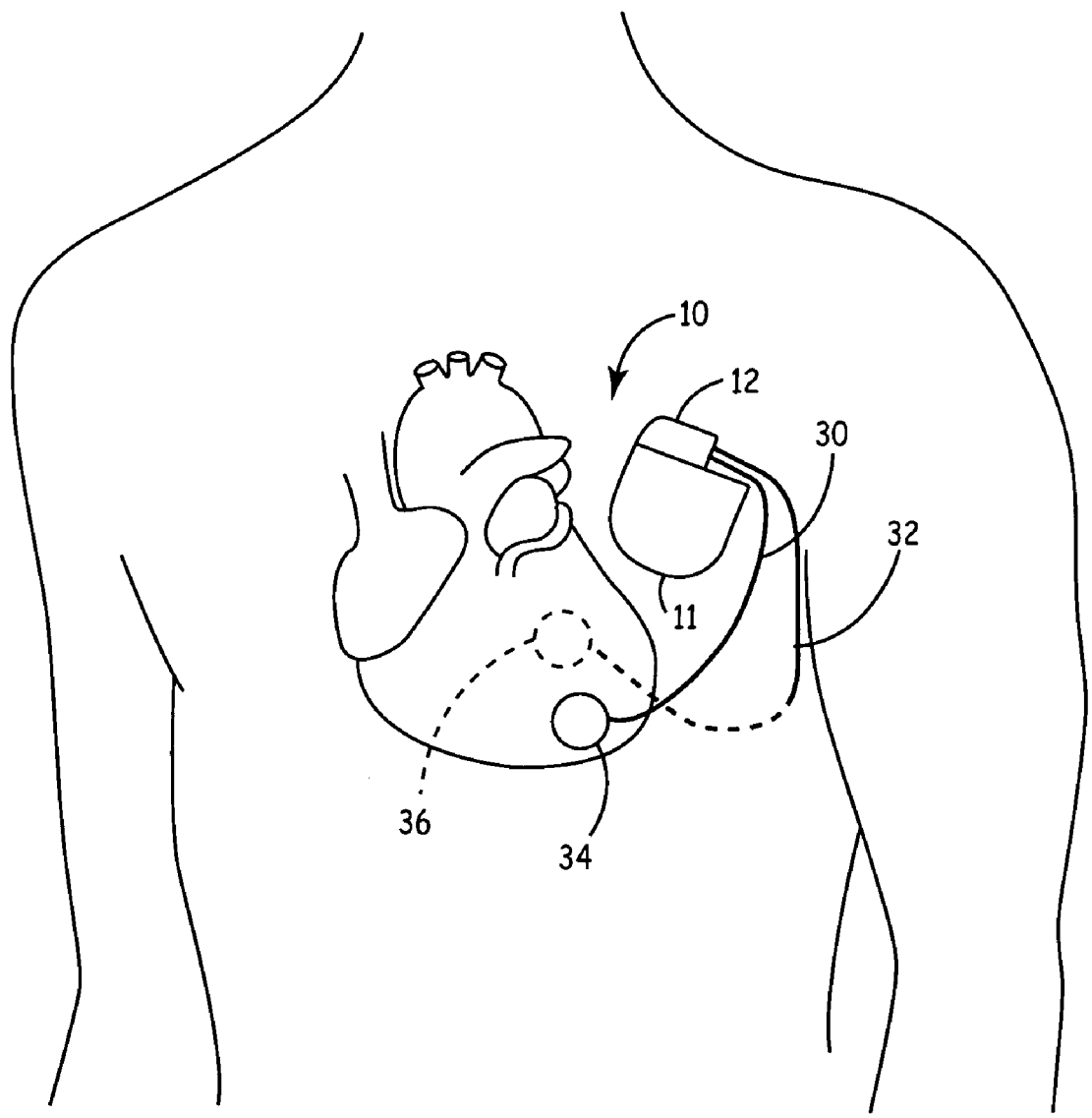
FIG. 1B is an illustration of an implantable cardiac stimulation device coupled to subcutaneous leads.

FIG. 1B is an illustration of an implantable cardiac stimulation device employing subcutaneous leads for positioning electrodes used for delivering defibrillation waveforms. In this embodiment, device 10 is coupled to two subcutaneous leads 30 and 32 coupled to subcutaneous patch electrodes 34 and 36, respectively. Subcutaneous patch electrodes 34 and 36 and device housing 11 may be positioned so that defibrillation pathways between the subcutaneous electrodes 34 and 36 and housing 11 will create an energy field encompassing a large mass of the targeted heart chambers.

In accordance with the present invention, phase-shifted or stepped defibrillation waveforms may be delivered along multiple pathways between subcutaneous electrodes 34 and 36 and housing 11 to create a multi-directional vector field. Sensing of cardiac activity may be performed using subcutaneous sensing electrodes (not shown) or electrodes incorporated on housing 11. It is recognized that additional electrodes dedicated to pacing and/or sensing functions may be incorporated on the device housing 11, subcutaneous patches 134 and 36 or on additional subcutaneous patches, also coupled to leads 30 or 32 or separate leads.

Positioning of device 10 is not limited to the left pectoral position, shown in FIG. 1B. For example, device 10 may alternatively be implanted in a right pectoral position. If housing 11 is not used as an electrode, device 10 may be implanted abdominally.

In alternative embodiments, a hybrid system including both subcutaneous electrodes and transvenous electrodes may be used. For example, transvenous leads may be used to position electrodes within the heart for accurate sensing of cardiac activity and subcutaneous electrodes may be positioned for delivering multi-directional defibrillation waveforms. The present invention may also be implemented in leadless subcutaneous cardiac stimulation devices such as the subcutaneous implantable cardioverter defibrillator generally disclosed in U.S. Pat. No. 6,647,292, issued to Bardy et al., incorporated herein by reference in its entirety.

Figure 2:
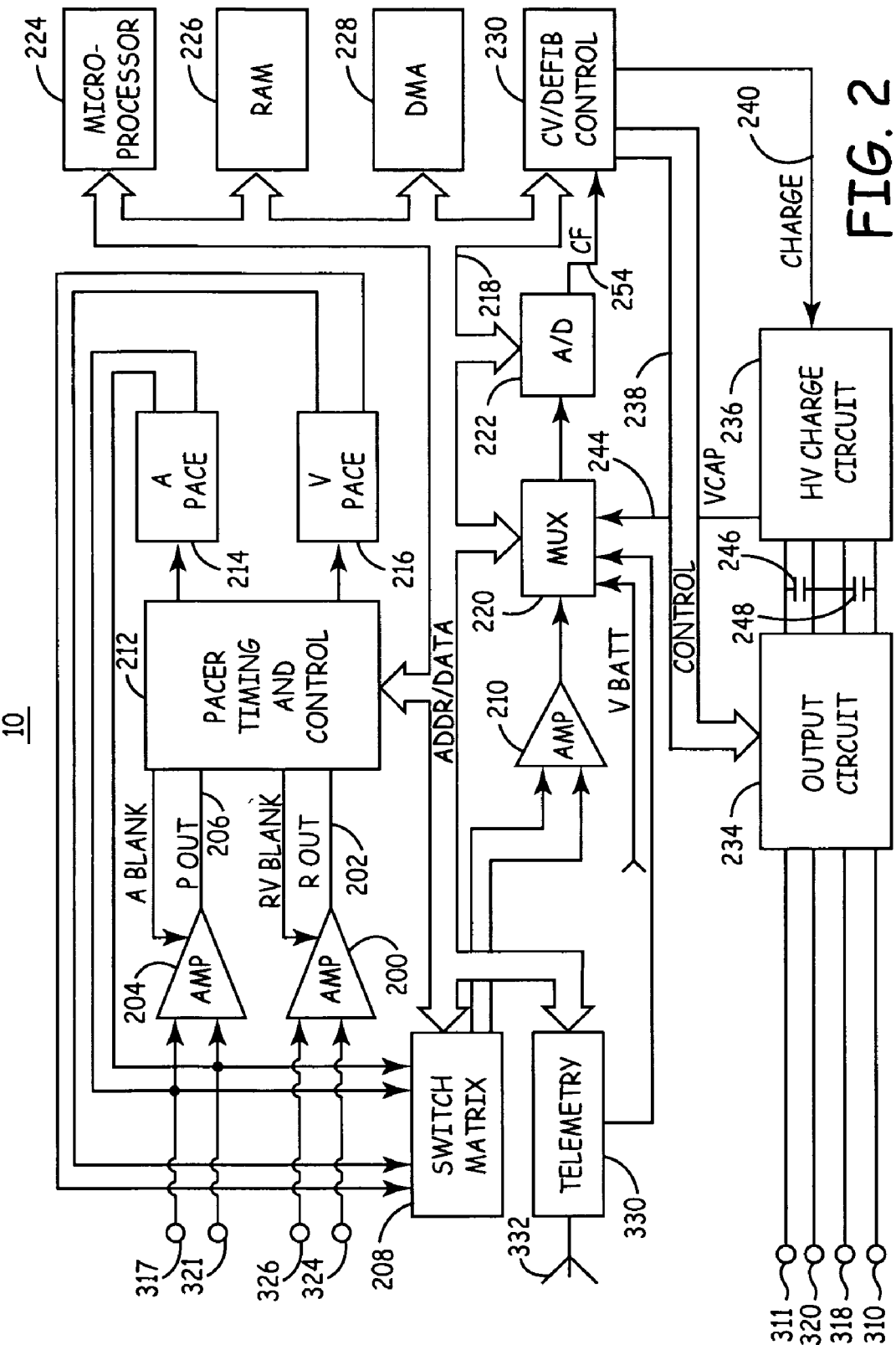
FIG. 2 is a functional block diagram of a cardiac stimulation device in which the present invention may be practiced.

FIG. 2 is a functional block diagram of the cardiac stimulation device shown in FIG. 1. This diagram should be taken as exemplary of the type of device with which the invention may be embodied and not as limiting, as it is believed that the invention may be usefully practiced in a wide variety of device implementations. For example, the present invention may be practiced in a device intended for delivering cardioversion and/or defibrillation shocks to one or more heart chambers and may or may not include other cardiac stimulation therapy capabilities, e.g., cardiac pacing therapies. The disclosed embodiment shown in FIG. 2 is a microprocessor-controlled device, but the methods of the present invention may also be practiced with devices employing dedicated integrated circuitry for controlling device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as an active electrode during defibrillation. The connection terminals 320, 310, and 318 provide electrical connection to coil electrodes 20, 8 and 23 respectively. Each of these connection terminals 311, 320, 310, and 318 may be located in connector block 12 and are coupled to the high voltage output circuit 234 to facilitate the delivery of high energy shocking pulses to the heart using coil electrodes 8, 20, and 23 and optionally the housing 11.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals such as R-waves.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228; Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern ICDs. Numerous types of telemetry systems known for use in implantable devices may be used.

The remainder of circuitry illustrated in FIG. 2 is dedicated to the provision of cardiac pacing, cardioversion and defibrillation therapies. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224. For the purposes of the present invention, pacer circuitry 212 may correspond to pacer timing and control circuitry known in the art.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, such as R-R intervals, P-P intervals and P-R intervals, which may be analyzed in response to a pace or sense interrupt by microprocessor 224 for diagnosing an arrhythmia. Any of the various arrhythmia detection methodologies known to the art may be employed for detecting ventricular and atrial arrhythmias.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. In the event that higher voltage cardioversion or defibrillation shock therapies are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. While a pair of capacitors 246 and 248 is shown in FIG. 2, the present invention may be implemented using a single high voltage capacitor or a bank of capacitors that includes two or more capacitors. When the capacitance voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation waveforms and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation waveforms and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman. Any known ventricular cardioversion or defibrillation control circuitry may be usable in conjunction with the present invention for controlling the timing of capacitor charging and delivery of cardioversion and defibrillation waveforms relative to sensed depolarization signals. Reference is made, for example, to U.S. Pat. No. 4,384,585, issued to Zipes and U.S. Pat. No. 4,949,719, issued to Pless et al.

In the illustrated device, delivery of cardioversion or defibrillation waveforms is accomplished by output circuit 234, under control of control circuitry 230 via control bus 238. Output circuit 234 determines the shock pulse waveform and which electrodes are involved in delivery of the shock waveform. In accordance with the present invention, output circuit 234 is provided as an output bridge including switching circuitry controlled by firmware resident in microprocessor 224 or by dedicated circuitry included in control circuit 230. As will be described in greater detail below, switching circuitry included in output circuit 234 is activated according to predetermined timing algorithms to produce phase-shifted waveforms.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. As in the case of currently available ICDs, and as discussed in the above-cited references, it is envisioned that the amplitude of the defibrillation shock waveform may be incremented in response to failure of an initial shock or shocks to terminate fibrillation. Prior art patents illustrating such pre-set therapy menus of anti-tachycardia therapies include U.S. Pat. No. 4,726,380 issued to Vollmann et al., U.S. Pat. No. 4,587,970 issued to Holley et al., and U.S. Pat. No. 4,830,006 issued to Haluska.

Figure 3A:
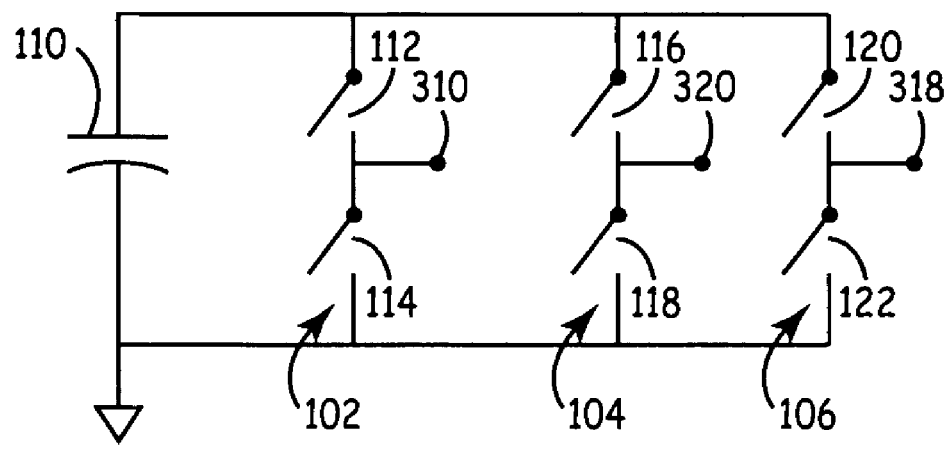
FIG. 3A is a diagram of an output bridge circuit that may be included in the cardioversion/defibrillation output circuitry shown in the device of FIG. 2, which may be used for generating a phase-shifted defibrillation waveform in accordance with the present invention for achieving a continuous multi-directional defibrillation vector field.

FIG. 3A is a diagram of an output bridge circuit that may be included in output circuit 234 for generating a phase-shifted defibrillation waveform for achieving a continuous multi-directional defibrillation vector field in accordance with the present invention. Bridge circuit 100 includes at least three legs 102, 104, and 106 coupled to a high voltage capacitor 110. Capacitor 110 may be embodied as a single capacitor element as shown in FIG. 3A or may be embodied as a bank of capacitors, including two or more capacitor elements such as the capacitors 246 and 248 shown in FIG. 2. When circuit 100 is used in conjunction with an external defibrillation device, capacitor 110 may conceivably be eliminated with the input to circuit 100 provided by line power.

Each leg 102, 104, and 106 includes a pair of switching components. Each pair is configured to include a "high" and a "low" switch for generating positive-going and negative-going pulse signals, respectively, for forming the positive- and negative-going phases of a defibrillation waveform. As will be described in greater detail below, control signals delivered to each pair of switching components 112 and 114, 116 and 118, and 120 and 122 produce a chopped waveform within a sinusoidal envelope to approximate a sinusoidal waveform at each output terminal 310, 320 and 318. In other embodiments, phasic signals may be produced by signals that ramp and decay, rise and fall exponentially, or otherwise alternate in a phasic manner.

Switching elements 112 and 114 included in leg 102 provide positive and negative going pulses, respectively, that contribute to the formation of a first signal of a phase-shifted defibrillation waveform at terminal 310, which may correspond to the SVC coil electrode terminal 310 as shown in FIG. 2. Switching elements 116 and 118 included in leg 104 provide positive and negative going pulses that form a second signal of a phase-shifted defibrillation waveform at terminal 320, which may correspond to the RV coil electrode terminal 320 shown in FIG. 2. Likewise, switching elements 120 and 122 included in leg 106 provide positive and negative going pulses that form a third signal of a phase-shifted defibrillation waveform at terminal 318, which may correspond to the CS coil electrode terminal 318 shown in FIG. 2. Alternatively, any of legs 102, 104, and 106 may be coupled to terminal 311 for using the device housing as a "CAN" electrode as described previously. In addition, any of legs 102, 104 and 106 may be coupled to two or more terminals such that two or more electrodes, for example housing 11 and SVC coil 23, are tied to the same potential during defibrillation.

Switching elements 112 through 122 may be embodied as semi-conductor elements, such as field effect transistors (FETs), insulated gate bipolar junction transistors (IGBTs), silicon controlled rectifiers (SCRs), Triac switches or other switching components for alternating the capacitor discharge signal between a high and low level to create pulses used to construct a phase-shifted defibrillation waveform. Depending on the implementation of switching elements 112 through 122, for example if SCR or Triac switches are used, a current interruption device, FET or IGBT, may be included in each leg 102, 104 and 106 to accommodate switching. Switching elements included in output circuit 100 may alternatively be embodied as other types of switches such as micro electromechanical system (MEMs) switches as generally disclosed in commonly assigned U.S. Pat. Appl. Publication No. 2002/0095187 to Thompson et al., hereby incorporated herein by reference in its entirety.

The direction (positive or negative) and width of the pulses generated at output terminals 310, 318, and 320 is controlled by timing algorithms executed by dedicated circuitry in control circuit 230 or by firmware in microprocessor 224 for selectively opening or closing switching elements 112 through 122 in a predetermined pattern to generate a desired phase-shifted waveform.

Figure 3B:
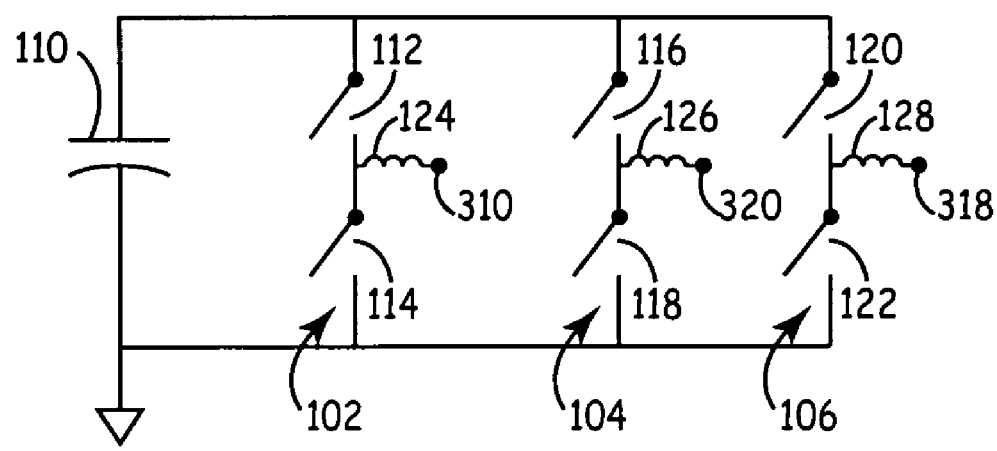
FIG. 3B is a diagram of an alternative output bridge circuit including choke elements.

In one embodiment, pulse width modulation (PWM) is performed to approximate a sinusoidal output from each leg 102, 104 and 106. A smoothed sinusoidal waveform may be produced by passing the PWM signal output of each pair of switching elements 112 and 114, 116 and 118, and 120 and 122 through a "choke" element 124, 126 and 128, respectively, as shown in the modified output bridge circuit 101 of FIG. 3B. Choke elements 124, 126 and 128 may be embodied as inductive circuit components, as shown in FIG. 3B, and serve to smooth the corners of the individual pulses included in a PWM signal to thereby form a smooth sinusoidal signal. While choke elements 124, 126 and 128 are shown in FIG. 3B to be included in bridge circuit 101, choke elements may alternatively be implemented outside bridge circuit 101, for example, in connector block 12 or in the leads carrying the defibrillation electrodes.

However, inductive elements 124, 126, and 128 may not be necessary to achieve reduced energy defibrillation using simultaneously delivered, phase-shifted defibrillation signals and may therefore be eliminated as shown previously in circuit 100 of FIG. 3A. In the embodiment of FIG. 3A, the heart tissue may act as a low pass filter to smooth the pulse width modulated signal to effectively produce a sinusoidal waveform through the defibrillation pathway.

Figure 4:
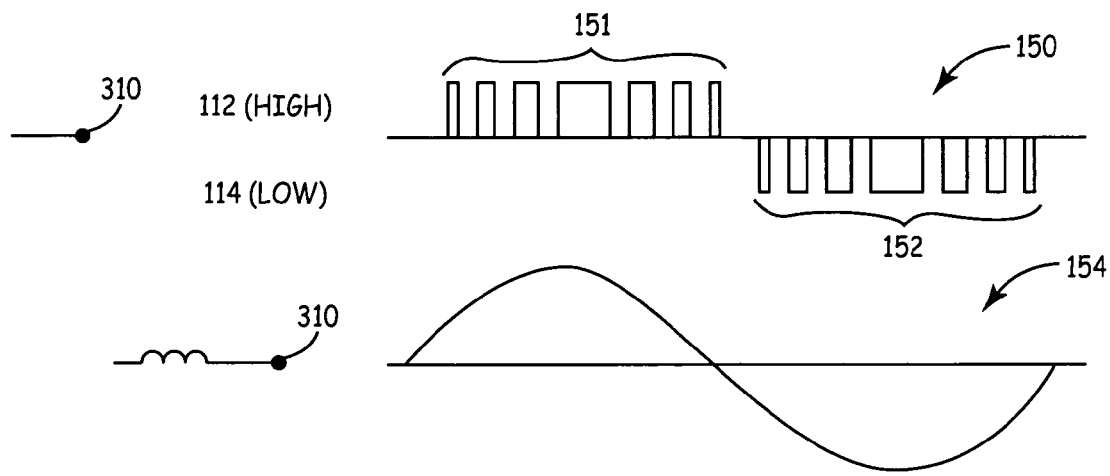
FIG. 4 is a conceptual illustration of a pulse width modulated output signal of any given leg of the output circuit of FIG. 3A, and the resulting sinusoidal waveform after applying a choke as in FIG. 3B.

FIG. 4 is a conceptual illustration of a PWM output signal of any given leg 102, 104, or 106, and the approximated sinusoidal waveform after applying a choke. With reference to leg 102, for example, the output of the "high" switching element 112 produces positive going pulses 151, and output of "low" switching element 114 produces negative going pulses 152 of pulse PWM signal 150. PWM signal 150 is shown containing several positive going pulses 151 and several negative going pulses 152 for the sake of illustration, however, it is recognized that PWM signal 150 may include a much larger number of pulses, for example 128, 256 or 512 pulses, of controlled pulse widths for forming a phasic signal. PWM signal 150 may be delivered to the heart via terminal 310 or smoothed using choke element 123 to deliver smoothed pulses within a sinusoidal envelope and thereby approximate a sinusoidal signal 154 at terminal 310.

Figure 5:
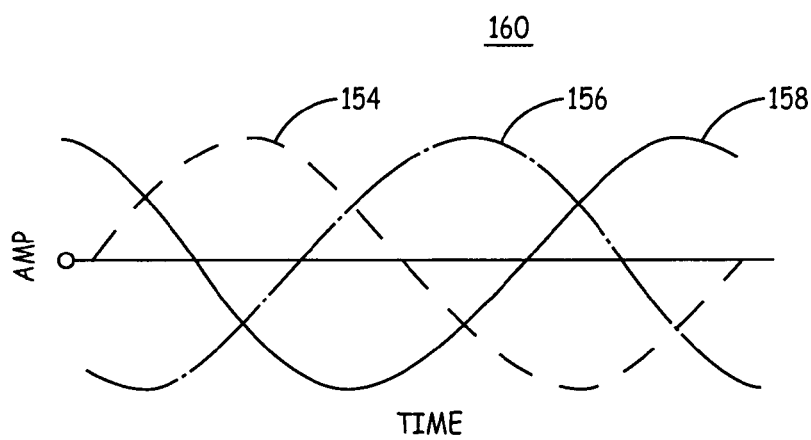
FIG. 5 is a plot of the resultant phase-shifted defibrillation waveform produced by the circuit of FIG. 3B.

FIG. 5 is a plot of the resultant phase-shifted waveform 160 produced by circuit 101. In the same manner as described in conjunction with FIG. 4, switching elements 116 and 118 of leg 104 produce positive and negative going pulses of a PWM signal, which may be smoothed to form an approximate sinusoidal signal 156 at terminal 320, and which is out of phase with sinusoidal signal 154 by a predetermined phase shift. The phase shift between signal 156 and signal 154 is controlled by the timing algorithm controlling the opening and closing of switching elements 116 and 118 and 112 and 114. A phase shift may be, for example, 120 degrees as shown in FIG. 5. Output of switching elements 120 and 122 produce a PWM signal, which is smoothed to form a sinusoidal signal 158, which is phase-shifted, e.g., 120 degrees, with respect to sinusoidal signal 156.

Each signal of the phase-shifted waveform 160 is applied simultaneously to respective electrodes, preferably positioned such that the majority of the targeted heart tissue is encompassed by the geometric space defined by the electrodes. For example, signal 154 may be applied to SVC coil electrode 23; signal 156 may be applied to RV coil electrode 20, and signal 158 may be applied to CS coil electrode 8. The three coil electrodes 8, 20 and 23 are arranged in a triangular manner, which may also be described as a Delta configuration, encompassing a large volume of the cardiac mass. The phase-shifted defibrillation waveform will result in a continuously rotating energy field. The continuous multi-directional field produces a more uniform defibrillation vector field, which is more efficient at depolarizing the heart since a greater mass of cells will be oriented perpendicularly to the energy field (at some point in time during the defibrillation waveform) compared to conventional defibrillation threshold vectors.

The phase-shifted defibrillation waveform may be particularly beneficial in subcutaneous defibrillation applications. Generally higher energy is required for achieving subcutaneous defibrillation than intracardiac defibrillation. The higher delivered voltage during subcutaneous defibrillation may give rise to tissue polarization problems. The lower voltage requirements and rotating field associated with a phase-shifted defibrillation waveform may reduce or eliminate tissue polarization problems that may otherwise be encountered using conventional defibrillation waveforms.

The output of each leg 102, 104, and 106 is shown shifted in phase by 120 degrees in FIG. 5. Phase shifts of greater or less than 120 degrees between each leg 102, 104, and 106 may alternatively be used in achieving a phase-shifted waveform. It is also recognized that while a three-phase waveform is achieved using the three-legged circuitry of FIG. 3A or 3B, additional legs may be provided for delivering four or more phase-shifted signals to four or more pathways.

Figure 6A:
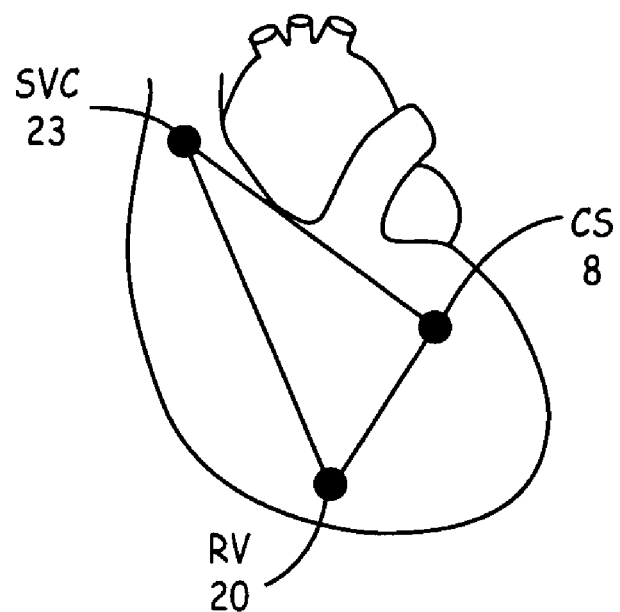
FIGS. 6A and 6B are schematic diagrams illustrating Delta and "Wye" electrode configurations, respectively, that may be used for delivering multi-directional defibrillation waveforms.
Figure 6B:
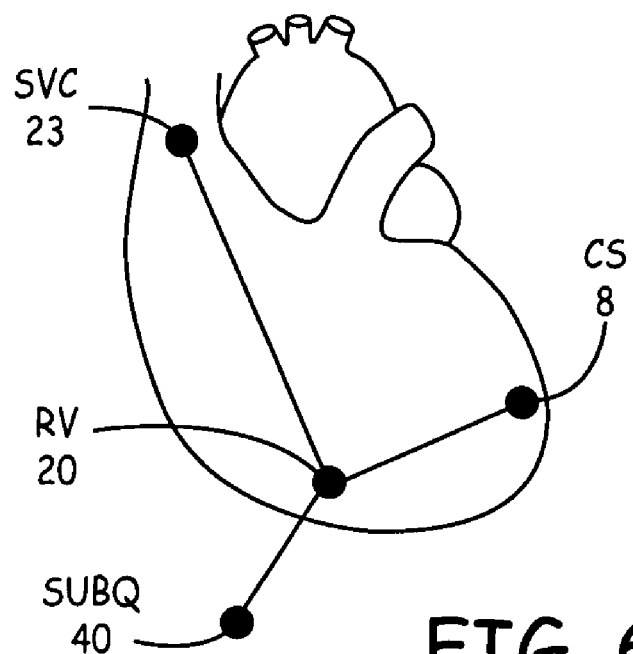

In alternative embodiments, an output bridge circuit may be coupled to defibrillation electrodes arranged in a "Wye" configuration rather than a Delta configuration as described above for delivering phase-shifted defibrillation waveforms. FIGS. 6A and 6B are schematic diagrams illustrating Delta and "Wye" electrode configurations, respectively, that may be used for delivering phase-shifted defibrillation waveforms. As described previously, three electrodes, e.g., RV coil electrode 20, SVC coil electrode 23 and CS coil electrode 8, may be used in a Delta configuration as shown in FIG. 7A. The triangle enclosed by the Delta configuration preferably produces an energy field encompassing a large mass of the targeted heart chambers.

In a "Wye" configuration, as shown in FIG. 6B, four electrodes are required wherein one electrode is the ground return for each of the other legs. In the example shown, the RV coil 20 may be the return electrode for three discharge paths provided by delivering the phase-shifted signals to SVC coil 23, CS coil 8 and a fourth electrode 40, which may correspond to the "CAN" electrode provided by housing 11 or a separately implemented subcutaneous or epicardial electrode. The fourth electrode 40 may be positioned relative to the ventricles so as to provide an additional current pathway not available with the three-electrode Delta configuration. Four-electrode configurations may be implemented using a fourth transvenous, intracardiac electrode as well.

Figure 6C:
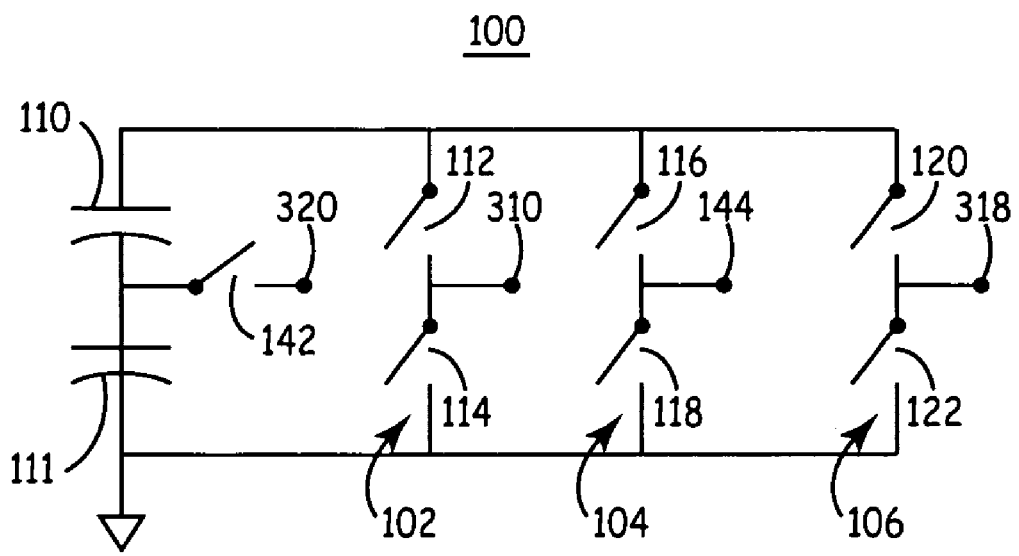
FIG. 6C is a circuit diagram of an output bridge circuit that may be used for achieving the "Wye" configuration shown in FIG. 6B.

FIG. 6C is a circuit diagram of an output bridge circuit that may be used for achieving the "Wye" configuration as shown in FIG. 6B. Output bridge circuit 140 includes an output terminal 320 coupled via a switching element 142 between a pair of capacitor elements 110 and 111. Output terminal 320 provides a common return path for the three legs 102, 104 and 106. Each of legs 102 and 106 include output terminals 310 and 318 coupled between switching elements 112 and 114 and 120 and 122 as described previously. Output leg 104 is shown to include output terminal 144 and switching elements 116 and 118 such that circuit 140 corresponds to the electrode arrangement shown in FIG. 6B. RV coil electrode 20 coupled to output terminal 320 provides a common return path for each of a subcutaneous electrode 40 (coupled to output terminal 144), CS coil electrode 8 (coupled to output terminal 318) and SVC coil electrode 23 (coupled to output terminal 310). Of course other arrangements of electrodes coupled to the output terminals of circuit 140 may be substituted for forming a "Wye" configuration using at least four electrodes.

Figure 6D:
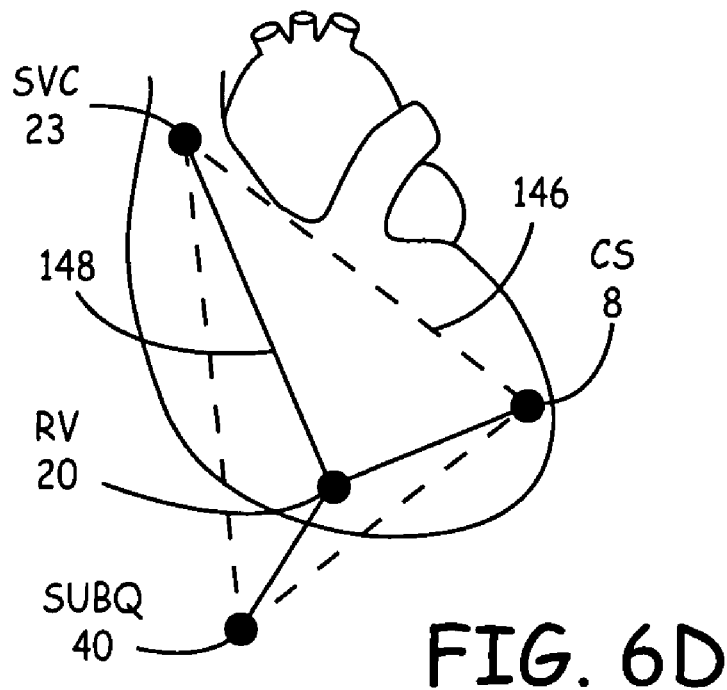
FIG. 6D is a schematic diagram illustrating Delta and "Wye" electrode configurations that may be achieved in alternation using the circuit of FIG. 6C.

By including switching element 142 for coupling output terminal 320 between capacitor elements 110 and 111, circuit 140 may also be used in Delta configuration by opening switching element 142. A Delta configuration would then exist between output terminal 310 (which may be coupled to SVC coil electrode 23), output terminal 144 (which may be coupled to subcutaneous electrode 40), and output terminal 318 (which may be coupled to CS coil electrode 8). The resulting Delta configuration is shown by dashed line in FIG. 6D. By alternating the state of switching element 142, the output configuration may alternate between a Delta configuration, indicated by dashed line in FIG. 6D, and a "Wye" configuration, indicated by solid lines in FIG. 6D. Thus, a different configuration may be selected for delivering defibrillation waveforms at different times, e.g. in response to different types of arrhythmia detections. Alternatively, the configuration may be alternated between "Wye" and Delta configurations during the delivery of a defibrillation waveform. If an initial shock of a shock sequence fails, the configuration may be changed by changing the state of switching element 142 on a subsequent shock.

Figure 7:
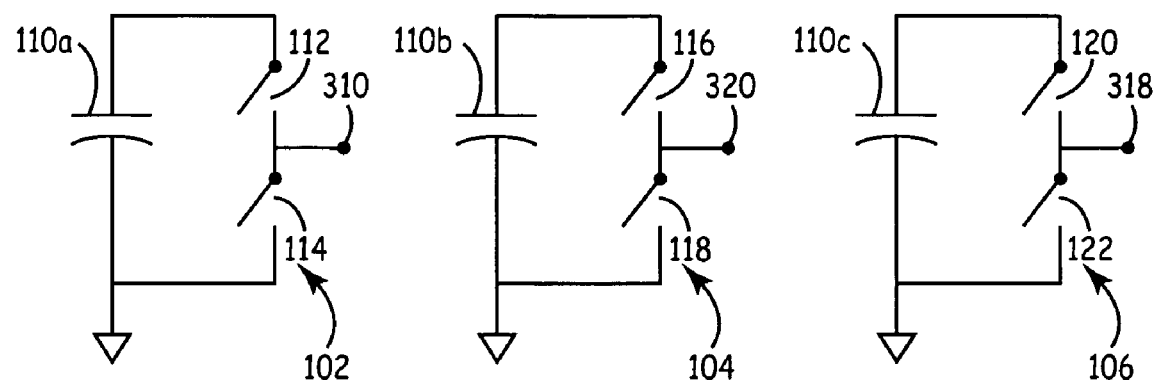
FIG. 7 is a circuit diagram of an alternative embodiment of output circuitry that may be used for delivering multi-directional defibrillation waveforms.

FIG. 7 is a circuit diagram of an alternative embodiment of output circuitry that may be included in output circuit 234. In some embodiments, one or more output legs may be provided, with each of the output legs including a separate designated capacitor to allow different voltage amplitudes to be applied to different output legs. In FIG. 6, each output leg 102, 104 and 106 is provided with a separate capacitor 110*a*, 110*b*, and 110*c*, respectively. While separate capacitors for each output leg are more costly and complex to implement than bridge circuits having only one capacitor, provision of separate voltage signals to each output leg 102, 104, and 106 may allow controlled current steering along the multiple defibrillation pathways. A higher capacitor voltage may be applied to a defibrillation pathway having higher resistance, for example due to a smaller electrode surface area, to obtain a desired current along that pathway. A more uniform or steered multi-directional field may thus be created by controlling the current delivered along the individual pathways.

Figure 8:
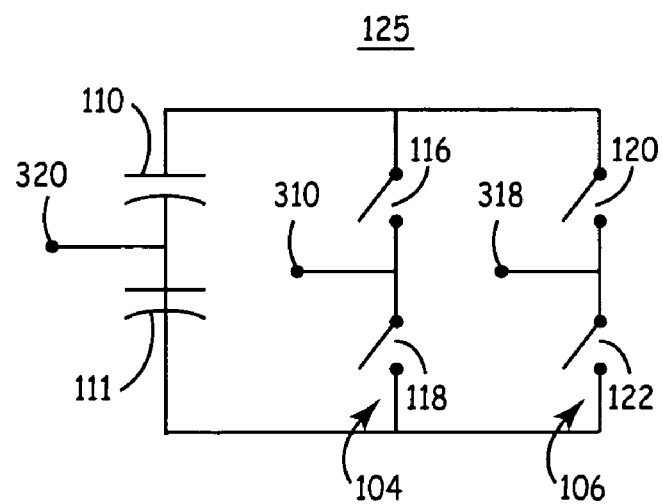
FIG. 8 is a circuit diagram of an alternative embodiment of an output bridge circuit having only two legs of switching circuitry, which may be used for delivering a multi-directional defibrillation waveform.

FIG. 8 is a circuit diagram of an alternative embodiment of an output bridge that may be included in output circuitry 234 for delivering a defibrillation waveform including simultaneously delivered phase-shifted signals for creating a continuous multi-directional vector field. The bridge circuit 125 is simplified by including only two legs of switching circuitry 104 and 106, each with an output terminal 310 and 318, with the third output terminal provided as a reference electrode between two capacitors 110 and 111. Two phase-shifted signals may be delivered to the output terminals 310 and 318 using the third terminal 320 as the return electrode. The two simultaneously delivered phase-shifted signals will produce a multi-directional vector field that will rotate in a continuous, sweeping fashion.

Figure 9A:
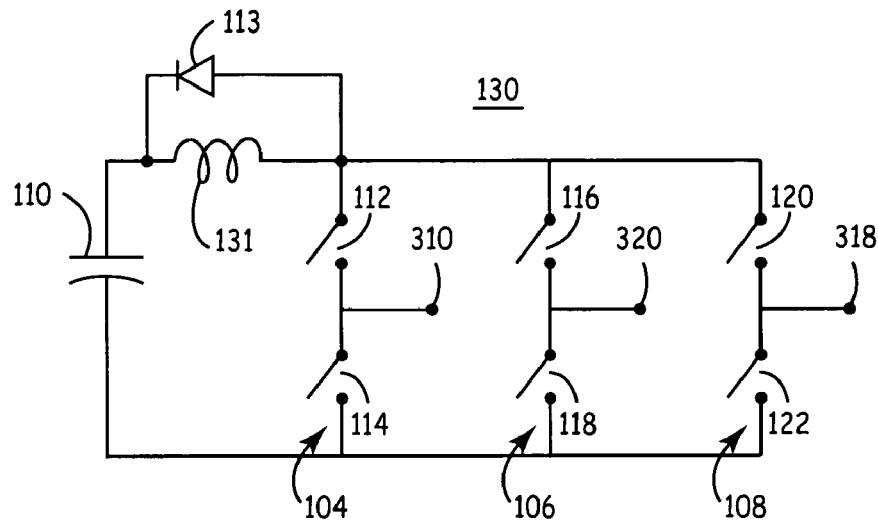
FIG. 9A is a circuit diagram of an embodiment of an output bridge circuit including a choke element in series with the high-voltage capacitor.

FIG. 9A is a circuit diagram of an embodiment of an output bridge circuit including a choke element in series with the high-voltage capacitor. In circuit 130, a choke element 131, such as an inductor, is positioned in series with capacitor 110 to smooth the leading edge of pulse signals generated at output terminals 310, 320, and 318. Positioning choke element 131 in series with capacitor 110 and before switching elements 112–122 creates a smoothing leading edge 134 as depicted in FIG. 9C that may be generated at any of the output terminals of circuit 130. By smoothing the leading edge, the pulse shape emulates a portion of a sine wave rather than the truncated exponential shape 136 normally achieved during capacitor 110 discharge without an in-series choke element 131.

As illustrated in FIG. 9A, a flyback diode 113 is positioned across the choking element 131 so that energy stored in the magnetic field of the inductor to return to the source capacitor when current flow is interrupted by opening the switches.

Figure 9B:
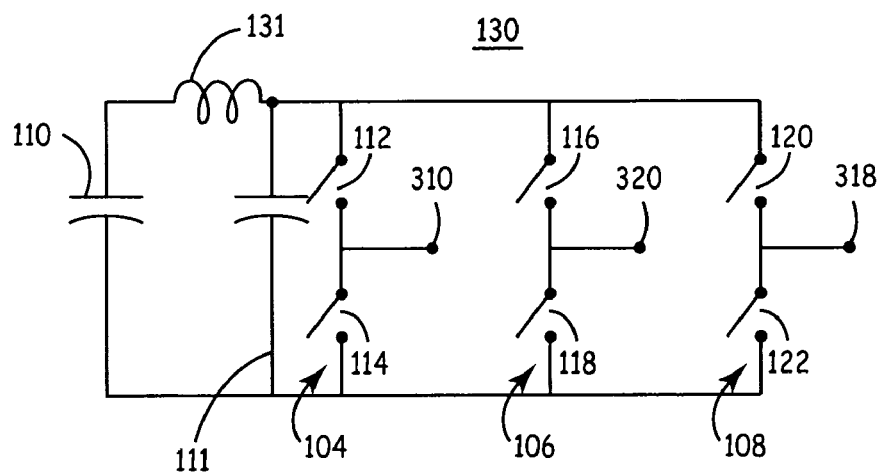
FIG. 9B is a circuit diagram of an embodiment of an output bridge circuit including a choke element in series with the high-voltage capacitor.
Figure 9C:
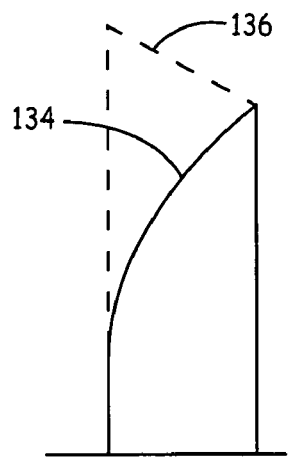
FIG. 9C is an illustration of a pulse signal having a smoothed leading edge that may be generated at any of the output terminals of the circuit shown in FIGS. 9A and 9B.

FIG. 9B is a circuit diagram of an embodiment of an output bridge circuit including a choke element in series with the high-voltage capacitor. As illustrated in FIG. 9B, according to an embodiment of the present invention, a second capacitor 111, which is a high voltage low capacitance capacitor, for example, is positioned across the output bridge instead of the flyback diode 113. This would have minimum effect on the desired smoothed output (FIG. 9C). When the switches open the energy stored in the magnetic field of the inductor would charge the capacitor across the output bridge.

In order to create the PWM signals used to generate an approximated sinusoidal waveform as described above, high-speed switching of switching elements 112 through 122 is required. Such high-rate switching of multiple switches for generating a PWM signal requires greater power and speed of control circuitry 230 or microprocessor 224 than for generating conventional biphasic or multiphasic pulse waveforms. As such, implementation of circuitry for producing PWM signals for approximating sinusoidal waveforms as described above is somewhat more complex than currently implemented circuitry for producing monophasic, biphasic or multiphasic truncated exponential waveforms, which require less switching power and lower speed. One advantage of the phase-shifted waveforms, however, may be significantly reduced defibrillation thresholds due to the continuous multi-directional vector field, which could more than offset the increased switching power requirements in terms of overall power savings and predicted device longevity.

Figure 10A:
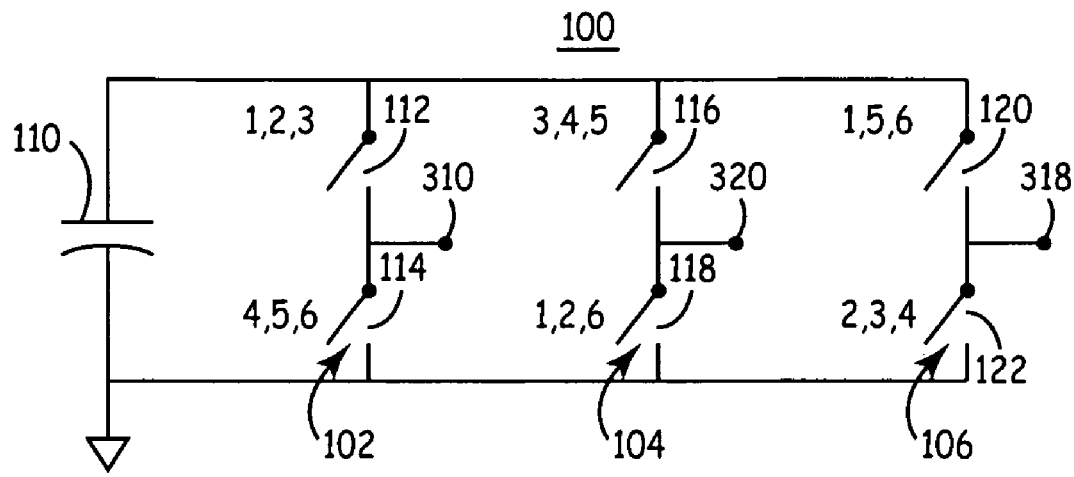
FIG. 10A is a circuit diagram and FIG. 10B is a corresponding timing diagram illustrating one method for generating a stepped, truncated exponential defibrillation waveform for achieving a discrete multi-directional defibrillation vector field.

Currently, implantable defibrillator output circuitry produces an exponentially decaying waveform (during capacitor discharge) that is truncated by output bridge switching circuitry to form the truncated exponential biphasic or multiphasic waveforms as described previously. FIG. 10A is a circuit diagram and FIG. 10B is a corresponding timing diagram illustrating a method for achieving a multi-directional defibrillation waveform that may be readily implemented in current defibrillator output circuitry.

A discrete multi-directional defibrillation waveform is achieved using output bridge circuitry currently implemented in implantable defibrillation devices using a timing control algorithm having a limited number of switching steps rather than the high-rate switching required to generate the PWM signals described above. In the embodiment shown in FIGS. 10A and 10B, six switching steps are applied to achieve a multivector defibrillation waveform. In FIG. 10A, the steps 1 through 6 during which each switching element 112, 114, 116, 118, 120 and 122 is opened are indicated next to the respective switching element. The resulting signals at the output terminals 310, 320 and 318 of each leg 102, 104, and 106, respectively, are shown in the timing diagram of FIG. 10B. These signals are the result of the exponentially decaying high voltage capacitor 110 discharge through the switching elements 112 through 120 as they are selectively opened or closed during the six steps as indicated in FIG. 10A.

The signal at terminal 310 of leg 102 is shown as pulse signal 402 which includes an exponentially decaying high signal for steps 1, 2 and 3 and an exponentially decaying low signal at steps 4, 5, and 6. The exponential signal at terminal 320 of leg 104 is shown as pulse signal 404 which includes a low signal at steps 1, 2 and 6, and a high signal at steps 3, 4, and 5. The exponential signal 318 of leg 106 is shown as pulse signal 406 which includes a high signal at steps 1, 5, and 6 and a low signal at steps 2, 3, and 4. As mentioned previously, depending on the implementation of switching elements 112 through 122, a current interruption device may be included in each leg 102, 104 and 106. In such implementations, the timing diagram of the stepped signals would include a separation time delay between switching steps.

Figure 10B:
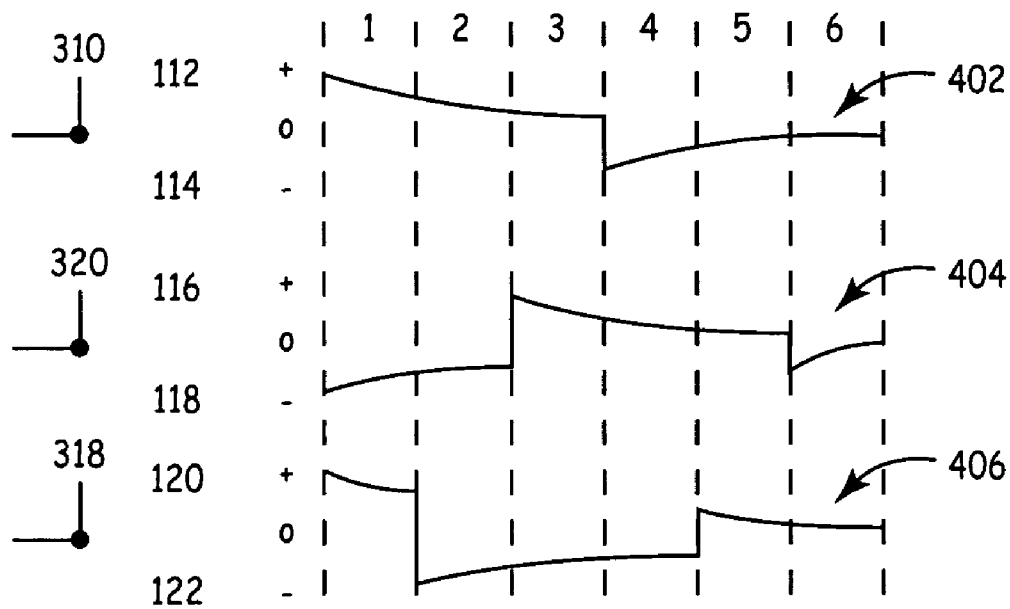
Figure 10C:
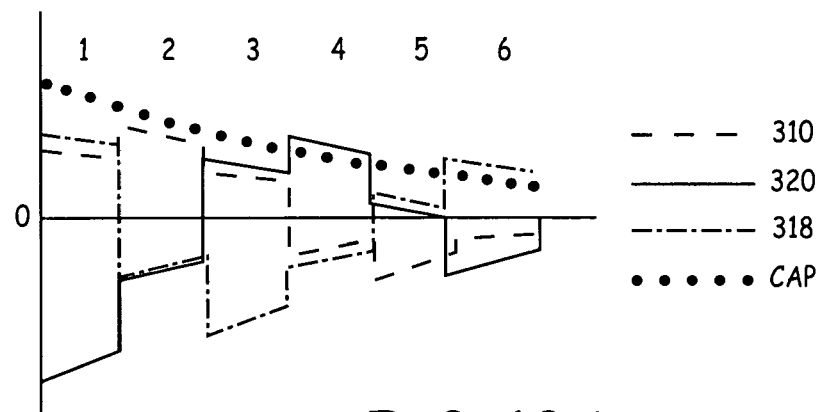
FIG. 10C is a plot of the current associated with each of the output terminals of the circuit of FIG. 10A, resulting from the six step signals shown in FIG. 10B, along with capacitor voltage as a reference.

FIG. 10C is a plot of the current associated with each output signal at terminals 310, 320 and 318 resulting from the six-step signals shown in FIG. 10B. The voltage on capacitor 110 is indicated by dotted line as a reference, and the current at each leg output terminal 310, 320 and 318 approximates a three-phase exponentially decaying defibrillation waveform. The duration of each step may be a predetermined duration of time or may be controlled based on the amount of capacitor discharge. In one embodiment, the multivector exponential waveform shown in FIG. 10C is 8.3 ms in duration with each of the six steps of equal duration.

Figure 11:
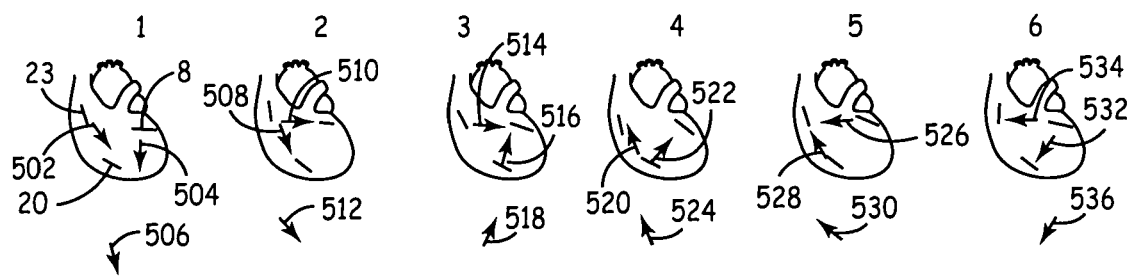
FIG. 11 is a schematic diagram illustrating a resultant multi-directional vector field applied to the heart during delivery of the 6-step, truncated exponential waveform of FIG. 10C.

The stepped defibrillation waveform of FIG. 10C will produce a discrete multi-directional defibrillation field that may be better comprehended by the diagram shown in FIG. 11. FIG. 11 is a schematic diagram illustrating the resulting vector field applied to the heart during delivery of the six-step defibrillation waveform shown in FIG. 10C. The vector diagrams shown in FIG. 11 correspond to the electrode arrangement shown in FIG. 1, wherein terminal 310 corresponds to SVC coil electrode 23, terminal 320 corresponds to RV coil electrode 20, and terminal 318 corresponds to CS coil electrode 8. However, it is to be understood that this electrode arrangement is merely exemplary and alternative electrode systems may be utilized with any of the phase-shifted or stepped defibrillation waveforms described above wherein the terminals 310, 318 and 320 of the output circuit 100 or 101 may be coupled to alternative defibrillation electrodes or combinations of electrodes which may be intracardiac, intravenous, epicardial, subcutaneous and/or submuscular electrodes with regard to implantable systems and may be cutaneous or transcutaneous with regard to external systems. Furthermore it is recognized that one or more electrodes may be tied to a single terminal. The positioning of electrodes and the device housing if used as a defibrillation electrode may be optimized as needed to achieve minimal defibrillation thresholds.

According to another embodiment of the present invention, an electrode configuration including RV coil 20, can 11, CS coil 8 and/or a coronary vein (CV) coil electrode could be utilized. CV coil 8 and the CV coil electrode could be utilized in conjunction with a pacing lead as electrically separate electrodes, tied together, or tied to RV coil 20 or can 11. In the dual coil configuration, a distal coil would be positioned within the coronary vein and a proximal coil would be positioned in the coronary sinus, and may be partially within the right atrium or the superior vena cava.

In step 1, outputs to terminal 310 (SVC coil 23) and 318 (CS coil 8) are high and output to terminal 320 (RV coil 20) is low. With regard to the electrode arrangement of FIG. 1, a defibrillation vector 502 between SVC coil electrode 23 and RV coil electrode 20 and a second vector 504 between CS coil electrode 8 and RV coil electrode 20 are produced simultaneously. The summation of these two vectors is approximated by the sum vector 506.

In step 2, output to terminal 310 (SVC coil 23) is high and outputs to terminals 320 (RV coil 20) and 318 (CS coil 8) are low producing vectors 508 and 510 from SVC coil 23 to RV coil 20 and CS coil 8 and the approximate sum vector 512. In step 3, output to terminals 310 and 320 are high and output to terminal 318 is low resulting in vectors 514 and 516 from SVC coil 23 and RV coil 20 to CS coil 8 and the approximate sum vector 518. In step 4, output to terminal 320 is high and outputs to terminals 310 and 318 are low producing vectors 520 and 522 and approximate sum vector 524. In step 5, outputs to terminals 320 and 318 are high and output to terminal 310 is low producing vectors 526 and 528 and approximate sum vector 530. Finally, in step 6, output to terminal 318 is high and outputs to terminals 310 and 320 are low producing vectors 532 and 534 and approximate sum vector 536.

Hence, the six-step defibrillation waveform produces a defibrillation field that rotates stepwise in a counter-clockwise direction as indicated by approximate sum vectors 506, 512, 518, 524, 530, and 536. In alternative embodiments, the switching steps selected to alternate high and low signals at each of terminals 310, 318 and 320 may be modified to produce a stepped waveform that produces a vector field that rotates in a generally clockwise direction or that rotates in an alternating or generally random order. The order of the switching steps as well as the starting and ending steps may be altered to vary the temporal and spatial variation of a discrete multi-directional vector field. Furthermore, any of the switching steps may be eliminated or repeated during defibrillation shock delivery. In summary, numerous modifications may be made to the stepped waveform shown in FIG. 10B to include any number of steps sequenced to create a multi-directional field that varies dynamically in stepwise changes, producing a desired temporal and spatial pattern of resultant defibrillation vectors.

Figure 12:
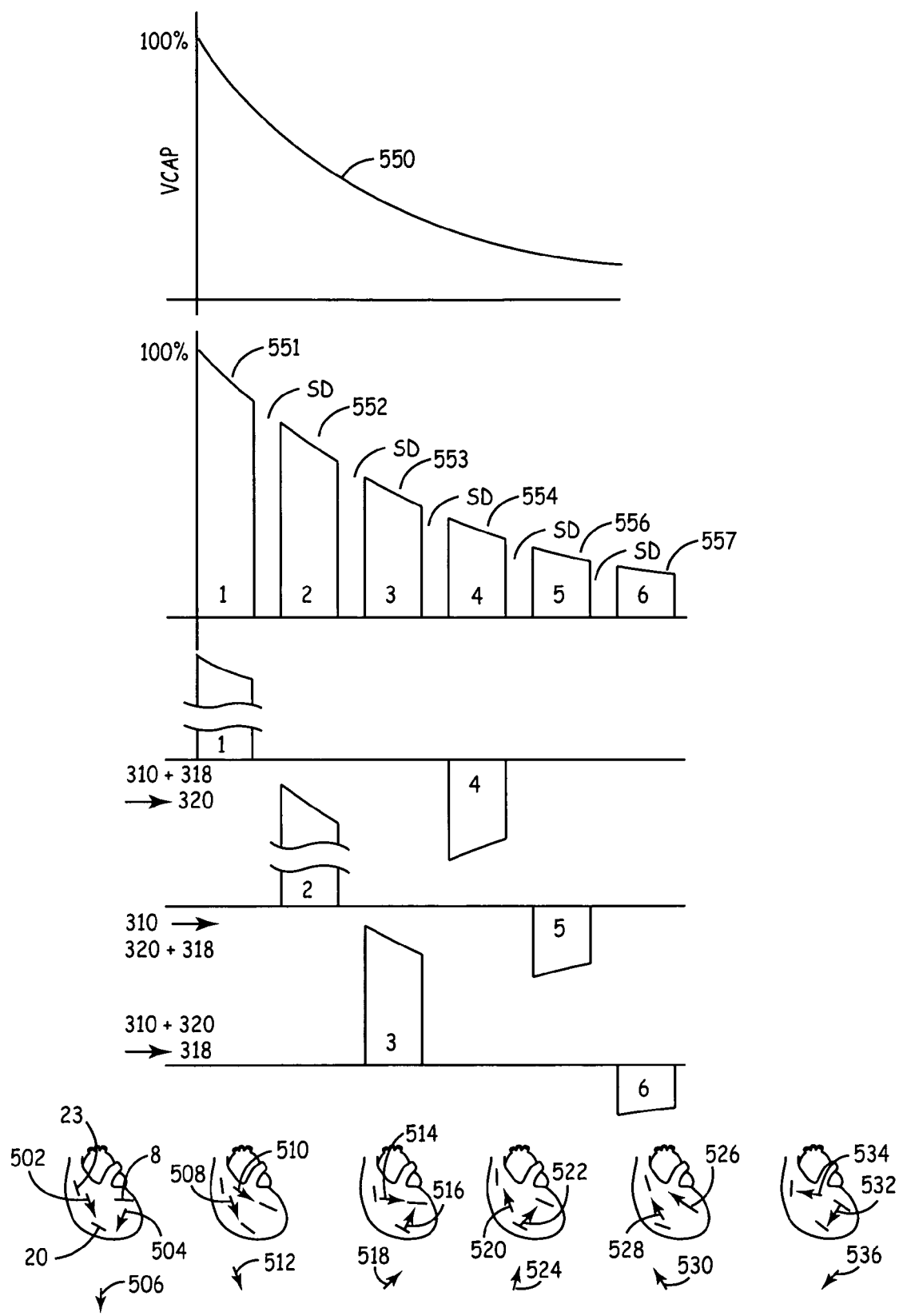
FIG. 12 is a timing diagram illustrating a method for achieving a discrete multi-directional waveform when switching delays are applied during capacitor discharge to create a sequence of pulses that are delivered sequentially to multiple pathways to create a rotational or other spatially-varying multi-directional field.

FIG. 12 is a timing diagram illustrating a method for achieving a discrete multi-directional waveform when switching delays are applied during capacitor discharge to create a sequence of pulses that are delivered sequentially to multiple pathways to create a rotational or other spatially-varying multi-directional field. Capacitor discharge voltage 550 is shown over time with corresponding discrete pulses 551 through 557 that may be formed by applying a switching delay (SD) at specified intervals during capacitor discharge. The resulting six discrete pulses 551 through 557 may be applied sequentially to desired multiple electrode pathways to achieve a discrete multi-directional field equivalent to that shown in FIG. 11.

Control signals may be applied to switches 112 through 122 of output bridge 100 to generate positive and negative going pulses at output terminals 310, 318 and 320 in a desired sequence to create a discrete multi-directional field. For the sake of illustration, terminal 310 may be coupled to SVC coil 23; terminal 320 may be coupled to RV coil 20, and terminal 318 to CS coil 8. In a first step, the "high" switches 112 and 120 of legs 102 and 106, respectively, and the "low" switch 118 of leg 104 are closed. Switches 114, 116, and 122 remain open. This combination of closed switches 112, 120 and 118 makes output terminals 310 and 318 positive with respect to output terminal 320 for the duration for pulse 551. Pulse 551 is thus delivered along pathways 502 and 504 creating the sum vector 506 in step 1.

When the duration for pulse 551 has expired, all switches 112 through 122 close, interrupting current flow for a switching delay interval (SD). This delay insures that both the "high" and "low" switches in any given leg cannot be "on" at the same time effectively preventing capacitor 110 from having a short circuit. Once an appropriate switching delay has been applied, the next pulse 552 can be delivered. To deliver pulse 552, the "high" switch 112 of leg 102 and the "low" switches 118 and 122 of legs 104 and 106, respectively, are closed. Switches 114, 116, and 120 remain open. This makes output terminal 310 positive with respect to output terminals 320 and 318 for the duration of pulse 552, creating defibrillation pathways 508 and 510 from SVC coil 23 to RV coil 20 and CS coil 8 producing sum vector 512.

The sequencing continues as shown in FIG. 12 until the waveform has been delivered. At step 3, output terminals 310 and 320 are positive relative to terminal 318. Pulse 553 is delivered along pathways 514 and 516, from SVC coil 23 and RV coil 20 to CS coil 8. Sum vector 518 is produced.

At step 4, the polarity of the output terminals is reversed compared to step 1. Output terminal 320 is positive relative to output terminals 310 and 318. "High" switching element 116 of leg 104 and "low" switching elements 114 and 122 of legs 102 and 106, respectively, are closed. Switches 112, 118, and 120 remain open. Pulse 554 is delivered along pathways 520 and 522 from RV coil 20 to SVC coil 23 and CS coil 8, producing the sum vector 524. Likewise, at steps 5 and 6, the opposite polarities at output terminals 310, 318 and 320 are created relative to step 2 and 3, respectively, resulting in sum vectors 530 and 536.

Note that it is not necessary to turn off all bridge switches during the switching delay interval (SD) between steps. Only an output bridge leg that is changing polarity, i.e., the "high" and "low" switches are changing state, needs to have both switches turned off for the switching delay to prevent a short circuit condition on capacitor 110.

Thus, a 6-step discrete multi-directional waveform is produced by delivering pulses 551 through 557 to the simultaneous pathways as indicated by arrows 502, 504, 508, 510, 514, 516, 520, 522, 526, 528, 532, and 534. The multi-directional waveform composed of sum vectors 506, 512, 518, 524, 530, and 536 rotates spatially in the same manner as the multi-directional field shown in FIG. 11.

A discrete multi-directional waveform may be formed by applying sequential pulses across multiple electrode pathways. The multi-directional defibrillation waveform generated according to the method shown in FIG. 12 by delivering pulses sequentially to multiple electrode pathways differs from prior known sequential pulse methods in that prior known methods generally involve delivering pulses along two single pathways sequentially rather than multiple pulses delivered simultaneously to multiple pathways in a sequential manner, including reversals in anode and cathode assignments.

Figure 13:
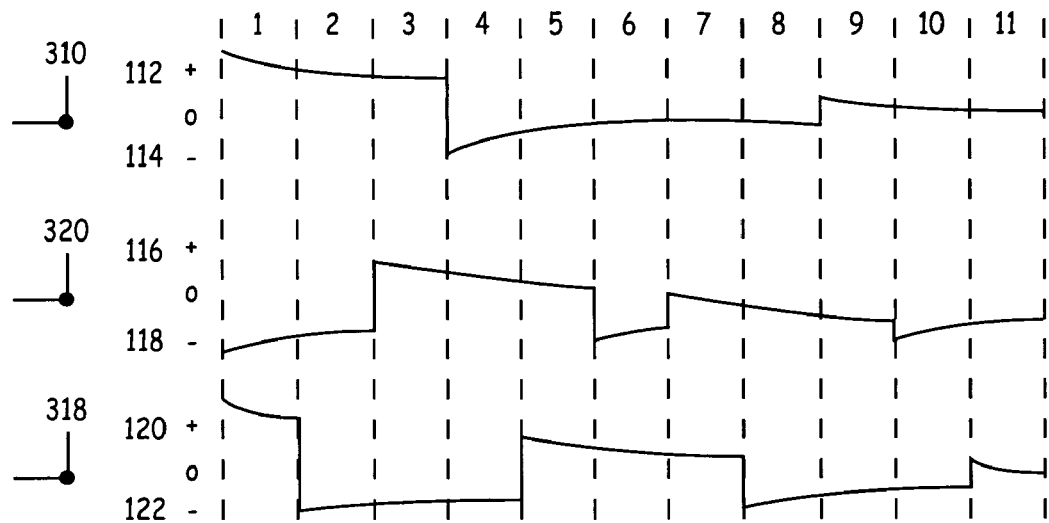
FIG. 13 is a timing diagram for an alternative method for delivering a stepped defibrillation waveform that includes 11 switching steps for achieving a discrete multi-directional defibrillation vector field.
Figure 14:
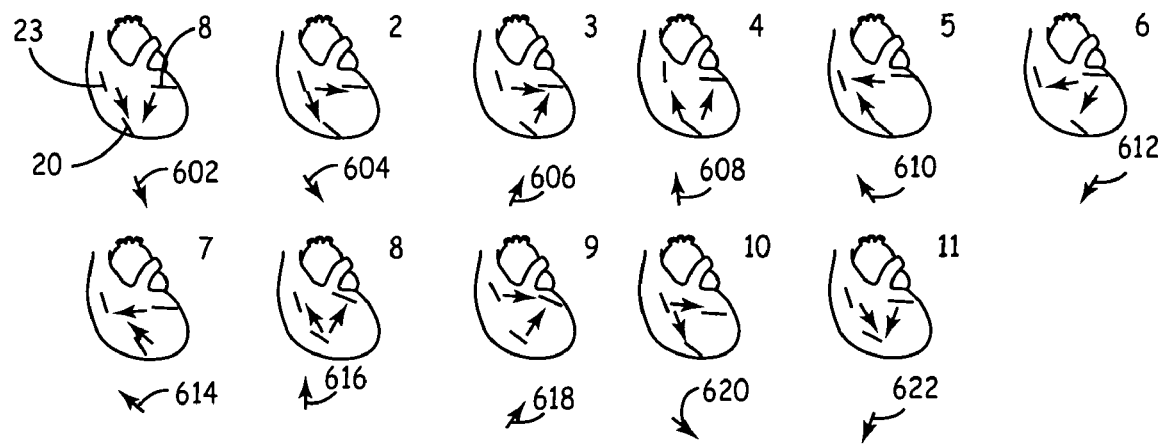
FIG. 14 is a diagram of the resultant vectors and approximate summation vectors produced during the 11-step truncated exponential defibrillation waveform of FIG. 13.

FIG. 13 is an alternative variation for delivering a stepped defibrillation waveform that includes 11 switching steps for achieving a discrete multi-directional vector field. Using the 11-step algorithm shown, a counter-clockwise discrete rotation of the defibrillation field followed by a clockwise discrete rotation of the defibrillation field can be achieved. The exponentially decaying signals produced at terminals 310, 320 and 318 are shown for each of the 11 steps in FIG. 13. The resultant vectors and approximate summation vectors produced when these signals are applied in an approximately triangular manner between SVC coil electrode 23, RV coil electrode 20 and CS coil electrode 8 are shown in FIG. 14.

Summation vectors 602 through 612 are seen to rotate in an approximately counter-clockwise direction while summation vectors 614 through 622 rotate in a generally clockwise direction. The switching steps shown in FIG. 13 may be modified to alter the rotation of the summation vectors 602 through 622 such that the summation vectors occur in a generally clockwise rotation followed by a generally counter-clockwise rotation or the summation vectors alternate between generally clockwise and counter-clockwise rotations or occur in a random order. In addition, the switching steps shown in FIG. 13 may be modified to eliminate or repeat any one of the summation vector steps and/or start or end at different vectors during the delivery of a multi-directional defibrillation waveform.

The 6-step defibrillation waveform and the 11-step defibrillation waveform illustrated in FIGS. 10B and 13, respectively, and the 6-step sequential pulse waveform of FIG. 12 illustrate the manner in which discrete multi-directional vector fields may be created using stepped defibrillation waveforms. It is recognized that numerous variations may be conceived in which a multi-directional vector changes direction in discrete steps in a temporal and spatial pattern that may be ordered or randomized. A multi-directional vector field that forms a complete rotation, partial rotation, multiple rotations, rotations in alternating directions or other ordered or randomized sequences may be created through designing the appropriate stepped signals to be delivered simultaneously across multiple electrode pathways.

Figure 15A:
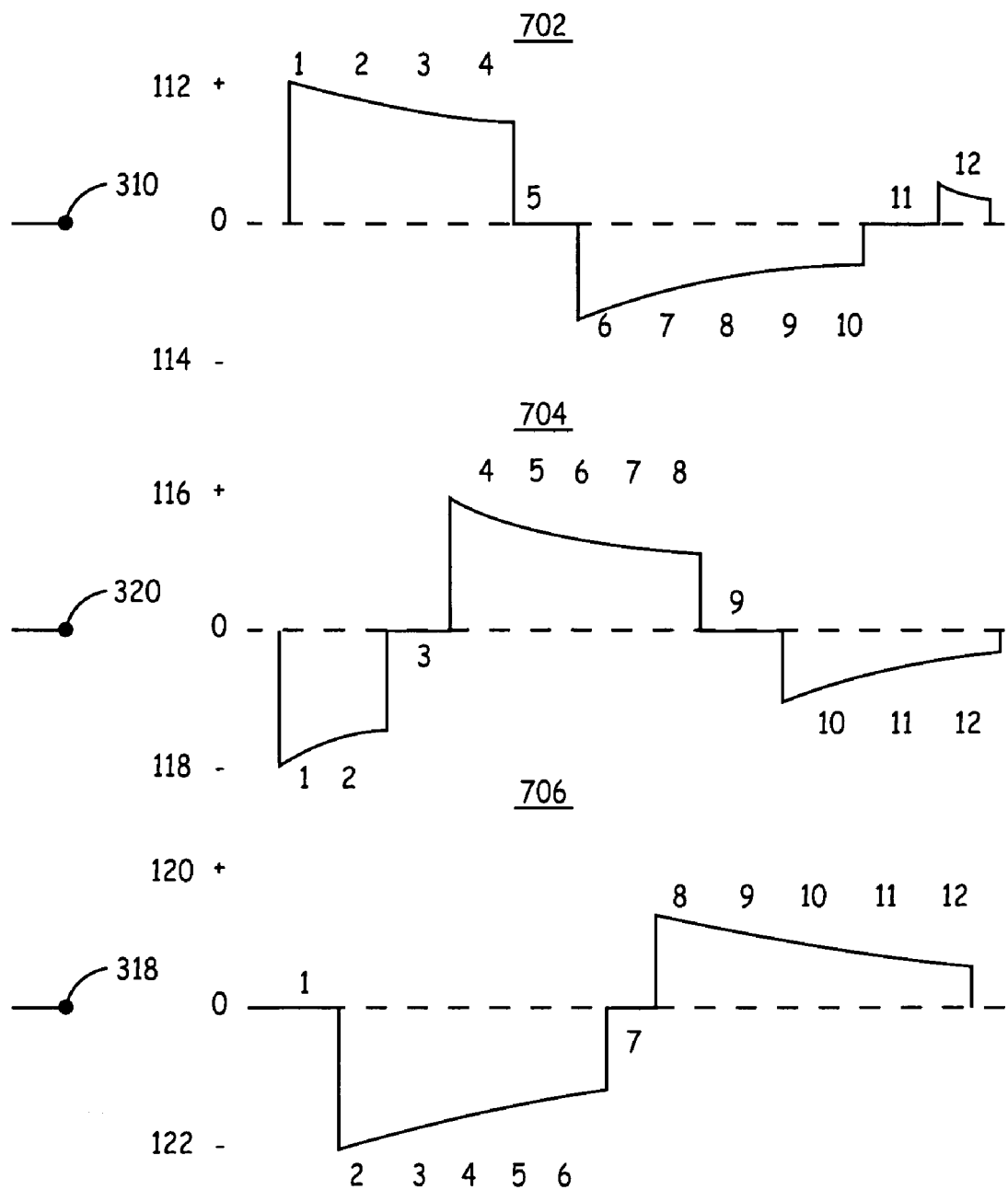
FIG. 15A is a timing diagram illustrating stepped switching signals included in a multi-directional defibrillation waveform that includes delays between switching steps that allow sequential delivery of stepped signals between multiple simultaneous pathways and single pathways.

FIG. 15A is a timing diagram illustrating a stepped switching algorithm that allows sequential delivery of stepped signals between multiple simultaneous pathways and single pathways. By including the delivery of stepped signals along both multiple simultaneous and single pathways, additional vectors may be added to a multidirectional vector field. In the 12-step waveform illustrated in FIG. 15A, an increased number of net vectors change direction in approximately 30 degree steps rather than approximately 60 degree steps as was the case for the 6-step waveform shown in FIG. 11. The smaller directional changes are accomplished by the addition of steps within a stepped defibrillation waveform resulting in pathways between single anode-to-cathode electrode pairs. For example, the voltage signals applied to terminals 310, 318, and 320 depicted in FIG. 15A will generate the steps 1 through 12 that create the resultant vectors 710 through 732 of FIG. 15B.

In FIG. 15A, a stepped signal 702 applied to terminal 310, which in this example is coupled to the SVC coil electrode 23, is positive going on steps 1 through 4 ("high" switch 112 is closed or "on" and "low" switch 114 is open or "off"). Switch 112 is opened at step 5 so that both switches 112 and 114 are open during step 5, removing terminal 310 from the output pathways. At step 6, "low" switch 114 is closed and remains closed through step 10 while switch 112 remains open. At step 11, switch 114 is opened, once again removing output terminal 310 from the output pathways. At step 12, switch 112 is closed while switch 114 remains open.

The stepped signal 704 applied to terminal 320, coupled to RV electrode 20 in this example, includes opening both "high" and "low" switches 116 and 118 at steps 3 and 9 to remove output terminal 320 from the output pathways during these steps. "Low" switch 118 is closed or "on" at steps 1, 2, 10, 11, and 12, and "high" switch 116 is closed or "on" during steps 4 through 8. The stepped signal 706 applied to terminal 318, coupled to CS electrode 8 in this example, includes opening both "high" switch 120 and "low" switch 122 at steps 1 and 7 to remove terminal 318 from the output pathways. "Low" switch 122 is closed during steps 2 through 6, and "high" switch 124 is closed during steps 8 through 12. Removing an output terminal from the output pathways on a given step by opening both switches of the corresponding output bridge leg allows defibrillation current to be applied along a single pathway between the other two output terminals.

Figure 15B:
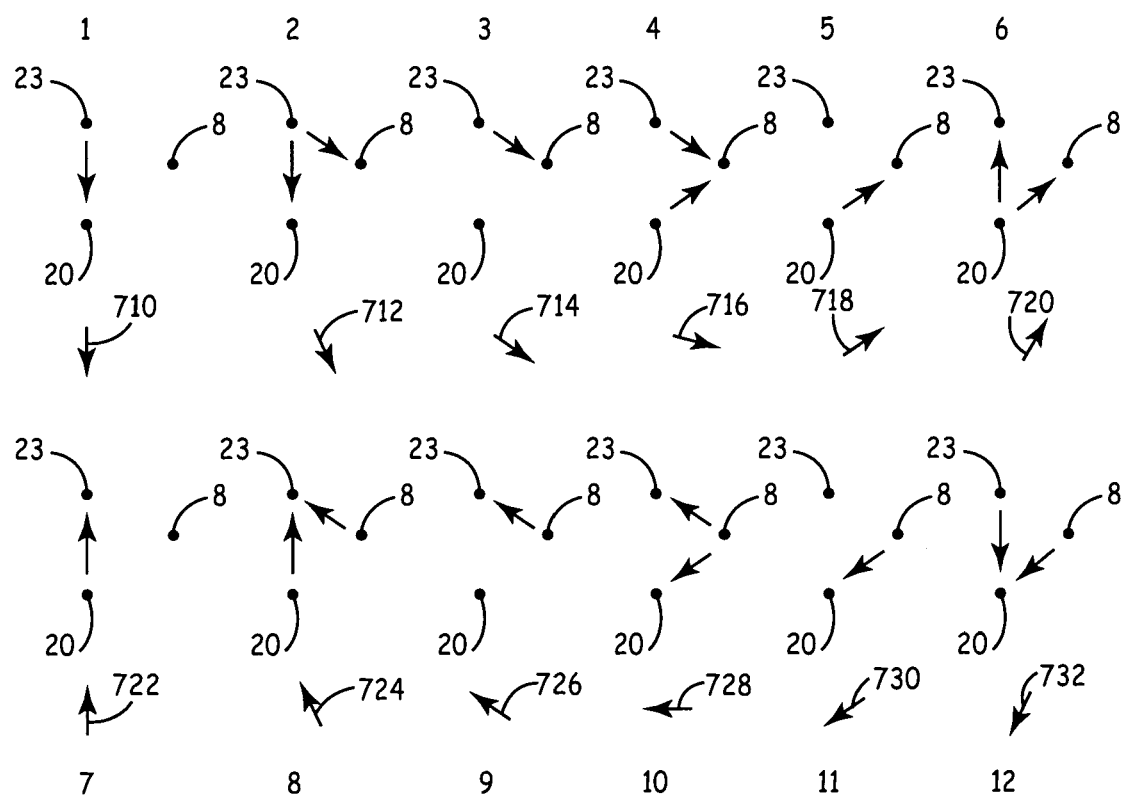
FIG. 15B is an illustration of the vector pathways applied during the 12-step defibrillation waveform of FIG. 15A and the resultant sum vectors are shown.

FIG. 15B is an illustration of the vector pathways applied during the 12-step switching algorithm of FIG. 15A, and the resultant sum vectors are shown. At steps 1, 3, 5, 7, 9, and 11, one of the output terminals 310, 318 or 320 is removed from the output pathways by opening both switching elements in the corresponding output leg. A pulse signal is then delivered along a single electrode pathway producing vectors 710, 714, 718, 722, 726, and 730. At steps 2, 4, 6, 8, 10, and 12, pulse signals applied simultaneously to all three output terminals produce dual pathway defibrillation vectors resulting in the approximate sum vectors 712, 716, 720, 724, 728, and 732 as shown.

Thus, the multi-directional defibrillation vector field is produced by alternating between dual pathway and single pathway vectors. The resultant multidirectional vector field rotates counterclockwise in approximately 30-degree steps rather than the larger, approximately 60 degree, steps as was shown for the 6-step algorithm of FIG. 11. Therefore, multidirectional defibrillation waveforms may include sequential delivery of stepped signals between single pathways and multiple simultaneous pathways.

Some of the techniques described above may be embodied as a computer-readable medium comprising instructions for a programmable processor such as microprocessor 224, output circuit 234 or control circuitry 212 shown in FIG. 2. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus, multi-directional defibrillation waveforms may advantageously be implemented in cardioversion/defibrillation devices to realize lower defibrillation thresholds, reduced device size and/or extended useful life. It is recognized that one of skill in the art, having the benefit of the teachings provided herein, may conceive of numerous variations or modifications to the embodiments described herein. For example, different types of continuous phasic signals may be delivered in a phase-shifted manner to a variety of multiple electrode configurations to achieve a continuous multi-directional defibrillation field. Discrete multi-directional defibrillation fields may be created using numerous variations of stepped waveforms delivered to a variety of electrode configurations. Therefore, while specific embodiments have been described to illustrate the various modes for practicing the invention contemplated to date, these illustrative embodiments are intended to be exemplary, rather than limiting with regard to the following claims.

What is claimed is:

1. A medical device for delivering a pulse waveform to a target site of a patient, comprising:
   an energy storage device storing electrical energy;
   a plurality of electrodes electrically coupled to the energy storage device;
   a plurality of switching elements coupled to the plurality of electrodes; and
   control circuitry, coupled to the plurality of switching elements, selectively switching the plurality of switching elements between a first state and a second state to direct discharge of the stored energy to be simultaneously output at selected electrodes of the plurality of electrodes to generate discrete sequential resultant output pulses across multiple pathways, the discrete sequential resultant output pulses generating a multi-directional waveform at the target site, wherein the multi-directional waveform generates a stimulation field that rotates stepwise in one of a clockwise direction and a counter-clockwise direction.

2. The device of claim 1, wherein the multi-directional waveform generates a stimulation field that rotates stepwise in one of a first direction corresponding to the stimulation field alternating between a clockwise direction and a counter-clockwise direction, and a second direction corresponding to the stimulation field randomly alternating between a clockwise direction and a counter-clockwise direction.

3. The device of claim 1, wherein the stimulation field rotates in one of a clockwise rotation followed by a counter-clockwise rotation, alternating between clockwise and counterclockwise rotations, and randomly rotating.

4. The device of claim 1, further comprising a smoothing element positioned in series with the energy storage device.

5. The device of claim 4, further comprising a diode positioned in parallel with the smoothing element.

6. The device of claim 4, further comprising a second energy storage device positioned between the smoothing element and the plurality of switching elements.

7. The device of claim 1, wherein the plurality of electrodes include a first electrode positioned within a right ventricle, a second electrode positioned within a superior vena cava, and a third electrode positioned within a coronary sinus.

8. The device of claim 1, further comprising a housing portion housing the energy storage device, the plurality of switching elements and the control circuitry, wherein the plurality of electrodes include a first electrode positioned within a right ventricle, a second electrode positioned along the housing portion, and a third electrode positioned in one of a coronary sinus and a coronary vein.

9. The device of claim 1, wherein the plurality of electrodes include one of an intracardiac electrode, an intravenous electrode, an epicardial electrode, a subcutaneous electrode a submuscular electrode, a cutaneous electrode, and a transcutaneous electrode.

10. The device of claim 1, wherein the control circuitry generates a delay of the simultaneous switching for a predetermined time period between generation of each of the discrete sequential resultant output pulses.

11. The device of claim 10, wherein the generation of the delay is associated only with pairs of switching elements of the plurality of switching elements to be switched between the first state and the second state.

12. The device of claim 10, wherein the multi-directional waveform generates a stimulation field that rotates stepwise in one of a first direction corresponding to the stimulation field alternating between a clockwise direction and a counter-clockwise direction, and a second direction corresponding to the stimulation field randomly alternating between a clockwise direction and a counter-clockwise direction.

13. The device of claim 10, wherein the stimulation field rotates in one of a clockwise rotation followed by a counter-clockwise rotation, alternating between clockwise and counterclockwise rotations, and randomly rotating.

14. The device of claim 10, further comprising a smoothing element positioned in series with the energy storage device.

15. The device of claim 14, further comprising a diode positioned in parallel with the smoothing element.

16. The device of claim 14, further comprising a second energy storage device positioned between the smoothing element and the plurality of switching elements.

17. The device of claim 10, wherein the plurality of electrodes include a first electrode positioned within a right ventricle, a second electrode positioned within a superior vena cava, and a third electrode positioned within a coronary sinus.

18. The device of claim 10, further comprising a housing portion housing the energy storage device, the plurality of switching elements and the control circuitry, wherein the plurality of electrodes include a first electrode positioned within a right ventricle, a second electrode positioned along the housing portion, and a third electrode positioned in one of a coronary sinus and a coronary vein.

19. The device of claim 10, wherein the plurality of electrodes include one of an intracardiac electrode, an intravenous electrode, an epicardial electrode, a subcutaneous electrode a submuscular electrode, a cutaneous electrode, and a transcutaneous electrode.

20. A medical device for delivering a pulse waveform to a target site of a patient, comprising:
   an energy storage device storing electrical energy;
   a plurality of electrodes electrically coupled to the energy storage device;

a plurality of switching elements coupled to the plurality of electrodes; and control circuitry, coupled to the plurality of switching elements, selectively switching the plurality of switching elements between a first state and a second state to direct discharge of the stored energy to be simultaneously output at selected electrodes of the plurality of electrodes to generate discrete sequential resultant output pulses across multiple pathways, the discrete sequential resultant output pulses generating a multi-directional waveform at the target site, wherein the multi-directional waveform has a duration approximately equal to 8.3 ms.

21. A method of delivering a pulse waveform to a target site of a patient, comprising:

sensing cardiac signals;

identifying a predetermined rhythm in response to the sensed signals; and simultaneously switching a plurality of switching elements between a first state and a second state to direct discharge of stored energy to be simultaneously output across multiple electrode paths to generate discrete sequential resultant output pulses in response to the identified predetermined rhythm, the discrete sequential resultant output pulses forming a multi-directional waveform at the target site, wherein the multi-directional waveform generates a stimulation field that rotates stepwise in one of a clockwise direction and a counter-clockwise direction.

22. The method of claim 21, wherein the multi-directional waveform generates a stimulation field that rotates stepwise in one of a first direction corresponding to the stimulation field alternating between a clockwise direction and a counter-clockwise direction, and a second direction corresponding to the stimulation field randomly alternating between a clockwise direction and a counter-clockwise direction.

23. The method of claim 21, wherein the discrete sequential resultant output pulses generate the multi-directional waveform by one of rotating in a clockwise rotation followed by a counter-clockwise rotation, alternating between clockwise and counterclockwise rotations, and randomly rotating.

24. The method of claim 21, wherein the plurality of switching elements are associated with electrodes including a first electrode positioned within a right ventricle, a second electrode positioned within a superior vena cava, and a third electrode positioned within a coronary sinus.

25. The method of claim 21, wherein the plurality of switching elements are associated with electrodes including a first electrode positioned within a right ventricle, a second electrode positioned along a device housing portion, and a third electrode positioned in one of a coronary sinus and a coronary vein.

26. The method of claim 21, further comprising generating a delay of the simultaneous switching for a predetermined time period between generation of each of the discrete sequential resultant output pulses.

27. The method of claim 26, wherein the generation of the delay is associated only with pairs of switching elements of the plurality of switching elements to be switched between the first state and the second state.

28. The method of claim 26, wherein the multi-directional waveform generates a stimulation field that rotates stepwise in one of a first direction corresponding to the stimulation field alternating between a clockwise direction and a counter-clockwise direction, and a second direction corresponding to the stimulation field randomly alternating between a clockwise direction and a counter-clockwise direction.

29. The method of claim 26, wherein the discrete sequential resultant output pulses generate the multi-directional waveform by one of rotating in a clockwise rotation followed by a counter-clockwise rotation, alternating between clockwise and counterclockwise rotations, and randomly rotating.

30. The method of claim 26, wherein the plurality of switching elements are associated with electrodes including a first electrode positioned within a right ventricle, a second electrode positioned within a superior vena cava, and a third electrode positioned within a coronary sinus.

31. The method of claim 26, wherein the plurality of electrodes include a first electrode positioned within a right ventricle, a second electrode positioned along a device housing portion, and a third electrode positioned in one of a coronary sinus and a coronary vein.

32. The method of claim 21, wherein simultaneously switching a plurality of switching elements between a first state and a second state comprises:

simultaneously generating a first pulse along a first vector and a second pulse along a second vector to generate a first resultant pulse;

simultaneously generating a third pulse along a third vector and a fourth pulse along the first vector to generate a second resultant pulse;

simultaneously delivering a fifth pulse along a fourth vector and a sixth pulse along the third vector to generate a third resultant pulse;

simultaneously delivering a seventh pulse along a fifth vector and an eighth pulse along the fourth vector to generate a fourth resultant pulse;

simultaneously delivering a ninth pulse along a sixth vector and a tenth pulse along the fifth vector to generate a fifth resultant pulse; and simultaneously delivering an eleventh pulse along the second vector and a twelfth pulse along the sixth vector to generate a sixth resultant pulse, wherein the resultant pulses generate a multi-directional waveform at the target site.

33. A computer-readable medium having computer-executable instructions for performing a method, comprising:

sensing cardiac signals;

identifying a predetermined rhythm in response to the sensed signals; and simultaneously switching a plurality of switching elements between a first state and a second state to direct discharge of deliver stored energy to be simultaneously output across multiple electrode paths to generate discrete sequential resultant output pulses in response to the identified predetermined rhythm, the discrete sequential resultant output pulses forming a multi-directional waveform at the target site, wherein the multi-directional waveform generates a stimulation field that rotates stepwise in one of a clockwise direction and a counter-clockwise direction.

34. An implantable medical device, comprising:

means for sensing cardiac signals;

means for identifying a predetermined rhythm in response to the sensed signals; and means for simultaneously switching a plurality of switching elements between a first state and a second state to direct discharge of stored energy to be simultaneously output across multiple electrode paths to generate discrete sequential resultant output pulses in response to the identified predetermined rhythm, the discrete sequential resultant output pulses forming a multi-directional waveform at the target site, wherein the multi-directional waveform generates a stimulation field that rotates stepwise in one of a clockwise direction and a counter-clockwise direction.

* * * * *